(12) United States Patent
Pendergrast et al.

(10) Patent No.: US 9,486,473 B2
(45) Date of Patent: Nov. 8, 2016

(54) MICRORNAS AND USES THEREOF

(71) Applicant: YMIR GENOMICS, LLC, Cambridge, MA (US)

(72) Inventors: P. Shannon Pendergrast, Cambridge, MA (US); R. Scott Pendergrast, Chatham, NJ (US); J. Stephen Pendergrast, Stockholm, NJ (US); Anna Irmina Markowska, Brookline, MA (US); Fred R. Huettig, Sudbury, MA (US)

(73) Assignee: YMIR Genomics, LLC, Cambridge, MA (US)

( * ) Notice: Subject to any disclaimer, the term of this patent is extended or adjusted under 35 U.S.C. 154(b) by 0 days.

(21) Appl. No.: 14/650,433

(22) PCT Filed: Dec. 10, 2013

(86) PCT No.: PCT/US2013/074055
§ 371 (c)(1),
(2) Date: Jun. 8, 2015

(87) PCT Pub. No.: WO2014/093305
PCT Pub. Date: Jun. 19, 2014

(65) Prior Publication Data
US 2016/0030461 A1 Feb. 4, 2016

Related U.S. Application Data

(60) Provisional application No. 61/736,717, filed on Dec. 13, 2012.

(51) Int. Cl.
| | |
|---|---|
| *C12Q 1/68* | (2006.01) |
| *C07H 21/02* | (2006.01) |
| *C07H 21/04* | (2006.01) |
| *A61K 31/7088* | (2006.01) |
| *G06F 19/22* | (2011.01) |

(52) U.S. Cl.
CPC ......... *A61K 31/7088* (2013.01); *C12Q 1/6883* (2013.01); *G06F 19/22* (2013.01); *C12Q 2600/112* (2013.01); *C12Q 2600/118* (2013.01); *C12Q 2600/142* (2013.01); *C12Q 2600/158* (2013.01); *C12Q 2600/178* (2013.01)

(58) Field of Classification Search
CPC .................. C12N 2310/11; C12N 15/113
See application file for complete search history.

(56) References Cited

FOREIGN PATENT DOCUMENTS

EP    2 497 835 A2    9/2012

OTHER PUBLICATIONS

Yang et al. (Nucleic Acids Research, 2010, vol. 38, D123-D130).*
Rajesh C. M. et al. "11 MicroRNAs: Master Regulators of Ethanol Abuse and Toxicity?", *Alcoholism: Clinical & Experimental Research*, vol. 34, No. 4, Jan. 26, 2010, pp. 575-587.
Meng F. et al.: "Epigenetic Regulation of miR-34a Expression in Alcoholic Liver Injury", *The American Journal of Pathology*, vol. 181, No. 3, Sep. 2012, pp. 804-817.
Vuppalanchi R. et al.: "Regulation of Hepatic Cytochrome P450 3A (CYP3A) Activity by Micrornas (MIRNAS)", *Hepatology*; 62nd Annual Meeting of the American-Association-For-The-Study-Of-Liver-Diseases (AASLD), vol. 54, No. Suppl. 1, Oct. 2011, p. 718A.
Pan Y. Z. et al.: "MicroRNAs Regulate CYP3A4 Expression via Direct and Indirect Targeting", *Drug Metabolism and Disposition*, vol. 37, No. 10, Jul. 6, 2009, pp. 2112-2117.
Bai S. et al.: "MicroRNA-122 Inhibits Tumorigenic Properties of Hepatocellular Carcinoma Cells and Sensitizes These Cells to Sorafenib", Journal of Biological Chemistry, vol. 284, No. 46, Sep. 2, 2009, pp. 32015-32027.
Ryu S. et al.: "Discovery of Novel Human Breast Cancer MicroRNAs from Deep Sequencing Data by Analysis of Pri-MicroRNA Secondary Structures", *PLOS One*, vol. 6, No. 2, Feb. 8, 2011, pp. e16403-e16403.
Oulas A. et al.: "Finding Cancer-Associated miRNAs: Methods and Tools", *Molecular Biotechnology*; Part B of Applied Chemistry and Biotechnology, vol. 49, No. 1, May 24, 2011, pp. 97-107.
Mendes N. D. et al.: "Current tools for the identification of miRNA genes and their targets", *Nucleic Acids Research*, vol. 37, No. 8, Mar. 18, 2009, pp. 2419-2433.
Qiao Y. et al.: "MiR-483-5p controls angiogenesis in vitro and targets serum response factor", *Febs Letters*, vol. 585, No. 19, Sep. 1, 2011, pp. 3095-3100.

* cited by examiner

*Primary Examiner* — Amy Bowman
(74) *Attorney, Agent, or Firm* — Cooley LLP; Matthew Pavao; Heidi A. Erlacher

(57) ABSTRACT

The present invention provides novel microRNAs and their uses.

2 Claims, 15 Drawing Sheets

Image is representative of n= 2 independent experiment

Image is representative of n= 1 independent experiment

* $p<0.05$ as compared to normal $n=1$
independent experiments repeated in triplicate Image is representative of n= 2 independent experiment; * p<0.01

FIG. 5B  a b

Image is representative of n= 2 independent experiment; *p<0.01

Image is representative of n= 2 independent experiment; * p<0.01

Image is representative of n= 3 independent experiment

Image is representative of n= 2 independent experiment; *p<0.01

Image is representative of n= 2 independent experiment; *p<0.05

Image is representative of n= 1 independent experiment

A

B

*p<0.01 as compared to normal n=1
independent experiments, repeated in triplicate Image is representative of n= 2 independent experiment Image is representative of *n= 1* independent experiment, repeated in triplicate Image is representative of *n= 1* independent experiment, repeated in triplicate Image is representative of n= 2 independent experiment; * p<0.05

Image is representative of n= 2 independent experiment; * p<0.01

Image is representative of n= 3 independent experiment; * p<0.05

SEQUENCE LISTING

<160> NUMBER OF SEQ ID NOS: 7

<210> SEQ ID NO 1
<211> LENGTH: 51
<212> TYPE: DNA
<213> ORGANISM: Homo sapiens

<400> SEQUENCE: 1
actggcacct gataacacct tctgatggag tgtgatagaa ggtgatctag t    51

<210> SEQ ID NO 2
<211> LENGTH: 21
<212> TYPE: DNA
<213> ORGANISM: Homo sapiens

<400> SEQUENCE: 2
tggagtgtga tagaaggtga t    21

<210> SEQ ID NO 3
<211> LENGTH: 71
<212> TYPE: DNA
<213> ORGANISM: Homo sapiens

<400> SEQUENCE: 3
tatatatatg gagtgtgtat atatgtgtgt ttattttata tacacacata tatacacact    60
ccatatatat a    71

<210> SEQ ID NO 4
<211> LENGTH: 22
<212> TYPE: DNA
<213> ORGANISM: Homo sapiens

<400> SEQUENCE: 4
tatggagtgt gtatatatgt gt    22

<210> SEQ ID NO 5
<211> LENGTH: 50
<212> TYPE: DNA
<213> ORGANISM: Homo sapiens

<400> SEQUENCE: 5
gaaaggagtg gagtgtggtt tggcagaaca actgcatttc acagcttttc    50

<210> SEQ ID NO 6
<211> LENGTH: 22
<212> TYPE: DNA
<213> ORGANISM: Homo sapiens

<400> SEQUENCE: 6
aggagtggag tgtggtttgg ca    22

<210> SEQ ID NO 7
<211> LENGTH: 24
<212> TYPE: DNA
<213> ORGANISM: Homo sapiens
<220> FEATURE:
<221> NAME/KEY: misc_feature
<222> LOCATION: (2)..(2)
<223> OTHER INFORMATION: "n is a,c,g, or t"
<220> FEATURE:
<221> NAME/KEY: misc_feature
<222> LOCATION: (7)..(7)
<223> OTHER INFORMATION: "n is a,c,g, or t"
<220> FEATURE:
<221> NAME/KEY: misc_feature
<222> LOCATION: (12)..(12)
<223> OTHER INFORMATION: "n is a,c,g, or t"
<220> FEATURE:
<221> NAME/KEY: misc_feature
<222> LOCATION: (17)..(17)
<223> OTHER INFORMATION: "n is a,c,g, or t"
<220> FEATURE:

-continued

```
<221> NAME/KEY: misc_feature
<222> LOCATION: (22)..(22)
<223> OTHER INFORMATION: "n is a,c,g, or t"

<400> SEQUENCE: 7
tncaccnttc tnatcancac tncc                                              24
```

MICRORNAS AND USES THEREOF

CROSS-REFERENCE TO RELATED APPLICATIONS

This application is a National Stage Application, filed under 35 U.S.C. §371, of International Application No. PCT/US2013/074055, filed on Dec. 10, 2013, claims priority to, and the benefit of, U.S. Provisional Application No. 61/736,717, filed Dec. 13, 2012, the contents of which are incorporated herein in their entireties.

INCORPORATION BY REFERENCE OF SEQUENCE LISTING

The contents of the text file named "YMIR-001N01US_SeqList_$_{ST}$25.txt," which was created on Aug. 11, 2015 and is 2 KB in size, are hereby incorporated by reference in their entirety.

FIELD OF THE INVENTION

The field of the invention relates to novel microRNAs and their uses.

BACKGROUND OF THE INVENTION

Chronic liver disease is marked by the gradual destruction of liver tissue over time. Several liver diseases fall under this category, including cirrhosis and fibrosis, the latter of which is often the precursor to cirrhosis. Cirrhosis is the result of acute and chronic liver disease and is characterized by the replacement of liver tissue by fibrotic scar tissue and regenerative nodules leading to a progressive loss of liver function. Fibrosis and nodular regeneration results in the loss of the normal microscopic lobular architecture of the liver. Fibrosis represents the growth of scar tissue resulting from, for example, infection, inflammation, injury, and even healing. Over time, the fibrotic scar tissue slowly replaces the normal functioning liver tissue resulting in a decreasing amount of blood flow to the liver leaving the liver incapable of fully processing nutrients, hormones, drugs, and poisons that are found in the bloodstream. More common causes of cirrhosis include alcoholism, hepatitis C viral infections, ingestion of toxins, and fatty liver, but many other possible causes also exist.

Once any cirrhosis or fibrosis has occurred in the liver, it is generally considered irreversible. Rather, conventional treatment focuses on preventing any further progression of cirrhosis in the liver and mitigating the complications that can arise from cirrhosis. In more advanced stages of cirrhosis, the only conventionally known treatment is a liver transplant. The American Liver Foundation estimates that over 300,000 people in the United States are hospitalized each year as a result of cirrhosis of the liver. It is also estimated that 18,000 people are in need of liver transplants.

Chronic liver disease can also lead to hepatocellular carcinoma (HCC). HCC is the fifth most common cancer worldwide and has the fourth highest mortality rate. Unlike patients with other cancers, such as lung cancer and breast cancers, more than 95% of HCC patients die within five years of being diagnosed with HCC. Although HCC is the subject of continuing investigation and its symptoms are well known, early-stage diagnosis of this disease remains difficult and the survival rate after diagnosis is very low (3%-5%).

Thus, there remains a great need for early diagnosis and treatment of these liver diseases.

SUMMARY OF THE INVENTION

The present invention provides an isolated nucleic acid comprising a sequence of a pri-miRNA, pre-miRNA, mir-RNA, miRNA*, anti-miRNA, or a miRNA binding site, or a variant thereof.

The nucleic acid may comprise (a) a sequence of any one of SEQ ID NOs: 1-6; (b) a RNA encoded by the nucleic acid of (a), where the RNA is identical in length to (a); (c) a sequence at least 70% identical to (a) or (b), where the sequence comprises at least 8 contiguous nucleotides; or (d) complement of (a), (b) or (c), where the complement is identical in length to the nucleic acid of (a), (b), or (c).

The present invention provides a probe comprising any nucleic acid described herein. The probe may comprise at least 8-22 contiguous nucleotides complementary to any one of SEQ ID NOs: 1-6.

The present invention provides a plurality of any probes debrided herein.

The present invention provides a composition comprising any plurality of probes debrided herein.

The present invention provides a cell line comprising any nucleic acid described herein.

The present invention provides a vector comprising any nucleic acid described herein.

The present invention provides a pharmaceutical composition comprising any nucleic acid described herein.

The present invention provides a kit comprising any nucleic acid described herein or any probes described herein.

The present invention provides a method of preventing, treating or alleviating a symptom of a liver disease or extrahepatic Hepatitis-linked disease in a subject by administering to the subject a therapeutically effective amount of a composition comprising any nucleic acid described herein. The method may further comprise administering to the subject an additional agent. The additional agent may be Miravirsen.

The present invention provides a method of diagnosing or predicting a risk of developing a liver disease in a subject by obtaining a sample from the subject; measuring the level of any nucleic acid described herein in the sample; and comparing the level of the nucleic acid in the sample to a reference value, where a difference between the level of the nucleic acid in the sample and the reference value indicates the presence or the risk of developing the liver disease in the subject.

The present invention provides a method of characterizing a liver disease in a subject by obtaining a sample from the subject; measuring the level of any nucleic acid described herein in the sample; and comparing the level of the nucleic acid in the sample to a reference value, where a similarity between the level of the nucleic acid in the sample and the reference value indicates a characteristic of the liver disease represented by the reference value in the subject.

The present invention provides a method of diagnosing or predicting a risk of developing a CYP3A4 associated disorder in a subject by obtaining a sample from the subject; measuring the level of any nucleic acid described herein in the sample; and comparing the level of the nucleic acid in the sample to a reference value, where a difference between the level of the nucleic acid in the sample and the reference value indicates the presence or the risk of developing the CYP3A4 associated disorder in the subject. Preferably, the CYP3A4 associated disorder is a liver disease.

The present invention provides a method of determining CYP3A4 level in a subject by obtaining a sample from the subject; measuring the level of a nucleic acid comprising SEQ ID NO: 1 or 2 in the sample; and determining CYP3A level in the sample, where the level of the nucleic acid in the sample indicates the CYP3A4 level.

The present invention provides a method of determining a dosing regimen of a drug in a subject by obtaining a sample from the subject; measuring the level of a nucleic acid comprising SEQ ID NO: 1 or 2 in the sample; and comparing the level of the nucleic acid in the sample to a reference value, where an increase in the level of the nucleic acid in the sample compared to the reference value indicates a higher dosing regimen than average required for the subject.

The present invention further provides a method of determining toxicity of a drug in a subject by obtaining a first sample from the subject; measuring a first level of a nucleic acid comprising SEQ ID NO: 1 or 2 in the first sample; administering the drug to the subject; obtaining a second sample from the subject measuring a second level of a nucleic acid comprising SEQ ID NO: 1 or 2 in the second sample; and comparing the second level of the nucleic acid in the second sample to the first level of the nucleic acid in the first sample, where an increase in the level of the nucleic acid in the second sample compared to the first sample indicates the tested drug is toxic.

The present invention provides a method of identifying a novel miRNA. The method comprises steps of a) searching in a deep sequencing database using a seed sequence of a known miRNA that is associated with at least one disease, where the seed sequence consists of at least 6 nucleotides; b) identifying a read sequence in the deep sequencing database, where 0 or 1 mismatch exists when the seed sequence is aligned against the first 12 non-adaptor nucleotides at the 5' end of the read sequence; c) searching human genome database using a fragment of the read sequence consisting of the seed sequence and 10-12 nucleotides of the read sequence extended from the 3' end of the seed sequence; d) identifying in the human genome database a target sequence, where the fragment of the read sequence 100% matches the target sequence; e) determining the presence of a hairpin in a query sequence, where the query sequence consists of the fragment of the read sequence and 50-100 nucleotides of the target sequence extended from both the 5' and 3' ends of the fragment of the read sequence; f) determining the position of the seed sequence relative to the terminal loop of the hairpin within the query sequence when the hairpin is present; and g) identifying a novel miRNA sequence, where the seed sequence is 20-35 nucleotides upstream or 0-10 nucleotides downstream of the terminal loop of the hairpin.

The liver disease of the present invention is selected from a group consisting of Hepatitis C, Hepatitis B, hepatocellular carcinoma, metastatic liver cancer, alcohol-induced liver disease, non-alcohol-induced liver disease, cirrhosis, diabetes-related liver damage, and Alcoholic Fatty Acid Liver Disease (AFLD). Preferably, the liver disease is Hepatitis C, Hepatitis B, or hepatocellular carcinoma.

The nucleic acid in any method of the present invention may comprise any one of SEQ ID NOs: 1-6.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

BRIEF DESCRIPTION OF THE DRAWINGS

FIGS. 5B(a) and 5B(b) are graphs showing relative levels of SRF in mimic transfected HEPG2 cells assayed by Western blot (a), and quantitative fold change (b).

DETAILED DESCRIPTION OF THE INVENTION

The present invention is based upon, in partial, the discovery of novel miRNAs and their precursors. Accordingly, the present invention provides isolated nucleic acid sequences, the pharmaceutical compositions thereof, and their uses.

Nucleic Acid

MicroRNAs (miRNAs or mirs) are short (17-24 nucleotides) RNAs found in almost every organism and that have a profound effect on gene expression. miRNAs function by binding to specific messenger RNAs (mRNAs). The majority of the specificity for this interaction is generated from the first eight nucleotides (5' side) of the miRNA, known as the seed sequence. This binding leads to alteration of the mRNA expression. It is estimated that >30% of all human mRNAs are regulated by miRNAs, including many genes that are directly linked to disease. Furthermore, specific miRNAs can be significantly deregulated in diseased tissue. It has also recently been discovered that many miRNAs can accumulate in extra-cellular spaces such as animal biofluids including blood, urine, and saliva. Thus, miRNAs have all the characteristics to make exceptional tools for tissue or biofluid disease diagnostics.

However, despite significant research, there are no commercial miRNA-based diagnostic assays and therapies available for any liver disease.

Using a novel deep scanning method of the present invention (YmirScan), novel miRNAs are identified from several high throughput sequencing databases of a total ~33 million reads from liver, liver cancer cell lines and some non-liver sources.

The present invention is related to an isolated nucleic acid comprising a sequence of a pri-miRNA, pre-miRNA, miRNA, miRNA*, anti-miRNA, or a miRNA binding site, or a variant thereof.

Figure 17:
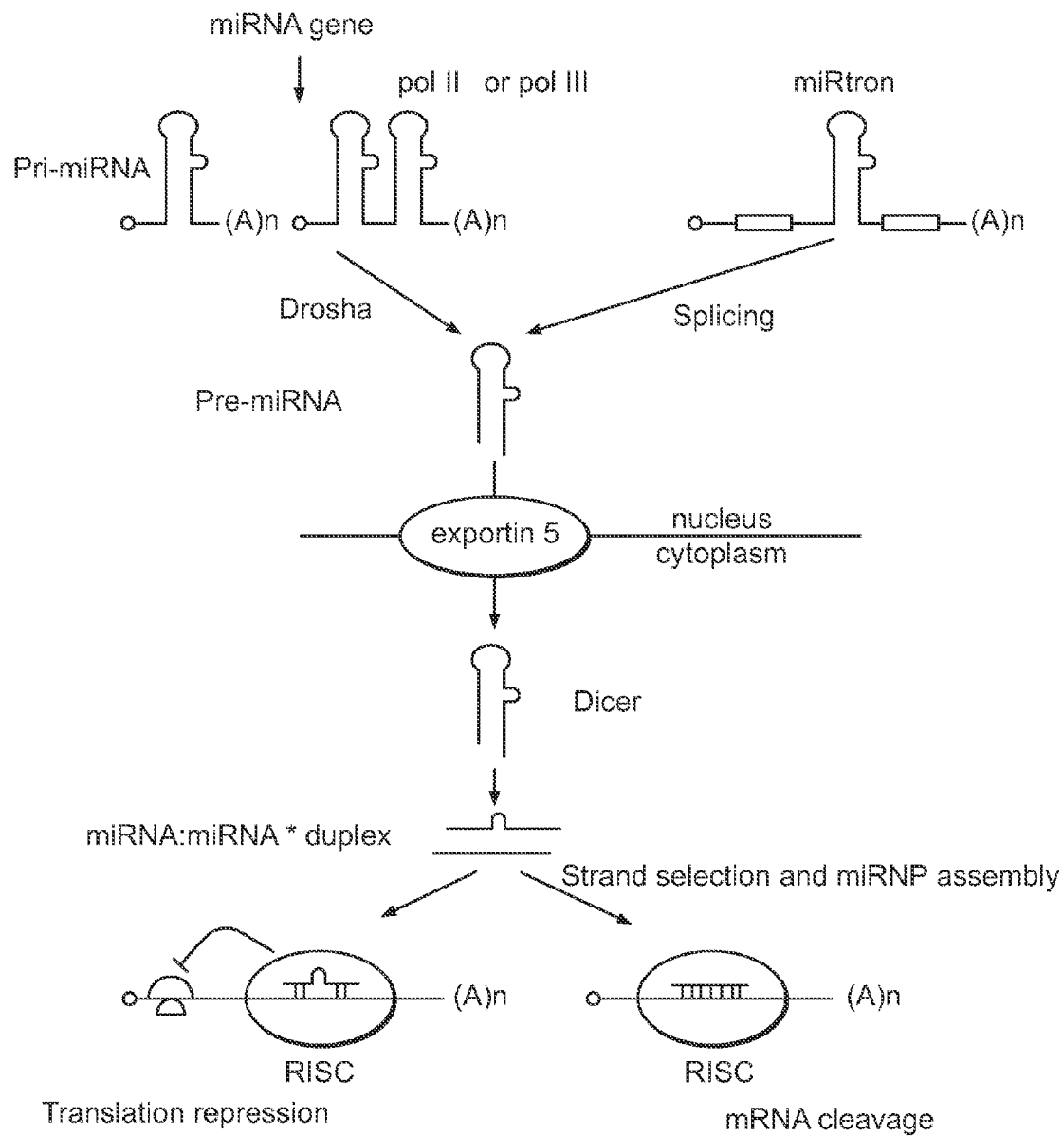
FIG. 17 is a graph showing the biogenesis and function of miRNAs.

While not being bound by theory, the current model for the maturation of mammalian miRNAs is shown in FIG. 17. A gene coding for a miRNA may be transcribed leading to production of an miRNA precursor known as the pri-miRNA. The pri-miRNA may be part of a polycistronic RNA comprising multiple pri-miRNAs. The pri-miRNA may form a hairpin with a stem and loop. As indicated on FIG. 17, the stem may comprise mismatched bases.

The hairpin structure of the pri-miRNA may be recognized by Drosha, which is an RNase III endonuclease. Drosha may recognize terminal loops in the pri-miRNA and cleave approximately two helical turns into the stem to produce a 60-70 nt precursor known as the pre-miRNA. Drosha may cleave the pri-miRNA with a staggered cut typical of RNase III endonucleases yielding a pre-miRNA stem loop with a 5' phosphate and ~2 nucleotide 3' overhang. Approximately one helical turn of stem (about10 nucleotides) extending beyond the Drosha cleavage site may be essential for efficient processing. The pre-miRNA may then be actively transported from the nucleus to the cytoplasm by Ran-GTP and the export receptor Ex-portin-5.

The pre-miRNA may be recognized by Dicer, which is also an RNase III endonuclease. Dicer may recognize the double-stranded stem of the pre-miRNA. Dicer may also recognize the 5' phosphate and 3' overhang at the base of the stem loop. Dicer may cleave off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. mRNA* sequences may be found in libraries of cloned miRNAs but typically at lower frequency than the miRNAs.

Although initially present as a double-stranded species with miRNA*, the miRNA may eventually become incorporated as single-stranded RNAs into a ribonucleoprotein complex known as the RNA-induced silencing complex (RISC). Various proteins can form the RISC, which can lead to variability in specifity for miRNA/miRNA* duplexes, binding site of the target gene, activity of miRNA (repress or activate), which strand of the miRNA/miRNA* duplex is loaded in to the RISC.

When the miRNA strand of the miRNA:miRNA* duplex is loaded into the RISC, the miRNA* may be removed and degraded. The strand of the miRNA:miRNA* duplex that is loaded into the RISC may be the strand whose 5' end is less tightly paired. In cases where both ends of the miRNA:miRNA* have roughly equivalent 5' pairing, both miRNA and miRNA* may have gene silencing activity.

The present invention relates to an isolated nucleic acid comprising a nucleotide sequence of any one of SEQ ID NOs: 1-6 or variants thereof.

| Composition name | Nucleic acid sequence | SEQ ID NO |
|---|---|---|
| Precursor #1 | ACTGGCACCTGATAACACCTTCTGATGGAGTGTG ATAGAAGGTGATCTAGT | 1 |
| miRNA #1 | TGGAGTGTGATAGAAGGTGAT | 2 |
| Precursor #2 | tatataTATGGAGTGTGTATATATGTGTgtttat tttatatacacacatatatacacactccatatat ata | 3 |
| miRNA #2 | TATGGAGTGTGTATATATGTGT | 4 |
| Precursor #3 | GAAAGGAGTGGAGTGTGGTTTGGCAGAACAACTG CATTTCACAGCTTTTC | 5 |
| miRNA #3 | AGGAGTGGAGTGTGGTTTGGCA | 6 |
| 7 | TXCACCXTTCTXATCAXCACTXCC, wherein X = any nucleotide | 7 |

"Nucleic acid" or "oligonucleotide" or "polynucleotide" used herein may mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid may be used for the same purpose as a given nucleic acid. Thus, a nucleic acid also encompasses substantially identical nucleic acids and complements thereof. As will also be appreciated by those in the art, a single strand provides a probe for a probe that may hybridize to the target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

A nucleic acid will generally contain phosphodiester bonds, although nucleic acid analogs may be included that may have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. Nos. 5,235,033 and 5,034,506, which are incorporated by reference. Nucleic acids containing one or more non-naturally occurring or modified nucleotides are also included within one definition of nucleic acids. The modified nucleotide analog may be located for example at the 5'-end and/or the 3'-end of the nucleic acid molecule. Representative examples of nucleotide analogs may be selected from sugar- or backbone-modified ribonucleotides. It should be noted, however, that also nucleobase-modified ribonucleotides, i.e. ribonucleotides, containing a non-naturally occurring nucleobase instead of a naturally occurring nucleobase such as uridines or cytidines modified at the 5-position, e.g. 5-(2-amino)propyl uridine, 5-bromo uridine; adenosines and guanosines modified at the 8-position, e.g. 8-bromo guanosine; deaza nucleotides, e.g. 7-deaza-adenosine; O- and N-alkylated nucleotides, e.g. N6-methyl adenosine are suitable. The 2'-OH-group may be replaced by a group selected from H, OR, R, halo, SH, SR, $NH_2$, NHR, $NR_2$ or CN, wherein R is $C_1$-$C_6$ alkyl, alkenyl or alkynyl and halo is F, Cl, Br or I. Modifications of the ribose-phosphate backbone may be done for a variety of reasons, e.g., to increase the stability and half-life of such molecules in physiological environments or as probes on a biochip. Mixtures of naturally occurring nucleic acids and analogs may be made; alternatively, mixtures of different nucleic acid analogs, and mixtures of naturally occurring nucleic acids and analogs may be made.

As used herein, an "isolated" or "purified" nucleic acid is substantially free of other nucleotides. Purified nucleic acids are also free of cellular material or other chemicals when chemically synthesized. Purified nucleic acids are at least 60% by weight (dry weight) the nucleic acids of interest. Preferably, the preparation is at least 75%, more preferably at least 90%, and most preferably at least 99%, by weight the nucleic acids of interest. For example, a purified nucleic acid is one that is at least 90%, 91%, 92%, 93%, 94%, 95%, 98%, 99%, or 100% (w/w) of the desired oligosaccharide by weight. Purity is measured by any appropriate standard method, for example, by column chromatography, thin layer chromatography, or high-performance liquid chromatography (HPLC) analysis. The nucleic acids are purified and used in a number of products for consumption by humans as well as animals, such as companion animals (dogs, cats) as well as livestock (bovine, equine, ovine, caprine, or porcine animals, as well as poultry). "Purified" also defines a degree of sterility that is safe for administration to a human subject, e.g., lacking infectious or toxic agents.

Similarly, by "substantially pure" is meant a nucleic acid that has been separated from the components that naturally accompany it. Typically, the nucleic acids are substantially pure when they are at least 60%, 70%, 80%, 90%, 95%, or even 99%, by weight, free from the proteins and naturally-occurring organic molecules with they are naturally associated.

The variant may be a complement of or substantially complementary to the referenced nucleotide sequence (i.e., SEQ ID NOs: 1-6). The variant may also be a nucleotide sequence that is substantially identical to the referenced nucleotide sequence or the complement thereof. The variant may also be a nucleotide sequence which hybridizes under stringent conditions to the referenced nucleotide sequence, complements thereof, or nucleotide sequences substantially identical thereto. The variant may also be identical in length of the referenced sequence. The referenced sequence may be the sequence with SEQ ID NO: 1, 2, 3, 4, 5, or 6. Preferably, the sequence is SEQ ID NO: 2, 4 or 6.

"Complement" or "complementary" as used herein may mean Watson-Crick or Hoogsteen base pairing between nucleotides or nucleotide analogs of nucleic acid molecules.

"Identical" or "identity" as used herein in the context of two or more nucleic acids or polypeptide sequences, may mean that the sequences have a specified percentage of nucleotides or amino acids that are the same over a specified region. The percentage may be calculated by comparing optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces staggered end and the specified region of comparison includes only a single sequence, the residues of single sequence are included in the denominator but not the numerator of the calculation. When comparing DNA and RNA, thymine (T) and uracil (U) are considered equivalent. Identity may be performed manually or by using computer sequence algorithm such as BLAST or BLAST 2.0.

"Stringent hybridization conditions" used herein may mean conditions under which a first nucleic acid sequence (e.g., probe) will hybridize to a second nucleic acid sequence (e.g., target), such as in a complex mixture of nucleic acids, but to no other sequences. Stringent conditions are sequence-dependent and will be different in different circumstances. Generally, stringent conditions are selected to be about 5-10° C. lower than the thermal melting point (Tm) for the specific sequence at a defined ionic strength pH. The Tm may be the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may be those in which the salt concentration is less than about 1.0 M sodium ion, typically about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, SxSSC, and 1% SDS, incubating at 42° C., or, SxSSC, 1% SDS, incubating at 65° C., with wash in 0.2×SSC, and 0.1% SDS at 65° C.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50 or more nucleotides or amino acids, or with respect to nucleic acids, if the first sequence is substantially complementary to the complement of the second sequence.

A "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with a nucleic acid sequence comprising any one of SEQ ID NOs: 1-6.

Alternatively, a "variant polynucleotide" or a "variant nucleic acid sequence" means a polynucleotide having at least about 60% nucleic acid sequence identity, more preferably at least about 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% nucleic acid sequence identity and yet more preferably at least about 99% nucleic acid sequence identity with a complement of the nucleic acid sequence comprising any one of SEQ ID NOs: 1-6.

The nucleic acid of the present invention may have a length of from 5 to 100 nucleotides. The nucleic acid of the present invention may have a length of at least 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 60, 70, 80 or 90 nucleotides. The nucleic acid of the present invention may be synthesized or expressed in a cell (in vitro or in vivo). The nucleic acid of the present invention may be synthesized as a single strand molecule and hybridized to a substantially complementary nucleic acid to form a duplex, which is considered a nucleic acid of the invention. The nucleic acid of the present invention may be introduced to a cell, tissue or organ in a single- or double-stranded form or capable of being expressed by a synthetic gene using methods well known to those skilled in the art, including as described in U.S. Pat. No. 6,506,559 which is incorporated by reference.

The nucleic acid of the present invention may comprise a sequence of a pri-miRNA or a variant thereof. The pri-miRNA sequence may comprise from 45-250, 55-200, 70-150 or 80-100 nucleotides. The sequence of the pri-miRNA may comprise a pre-miRNA, miRNA and miRNA*. The pri-miRNA may also comprise a miRNA or miRNA* and the complement thereof, and variants thereof. The pri-miRNA may comprise at least 19% adenosine nucleotides, at least 16% cytosine nucleotides, at least 23% thymine nucleotides and at least 19% guanine nucleotides.

The pri-miRNA may form a hairpin structure. The hairpin may comprise a first and second nucleic acid sequence that are substantially complimentary. The first and second nucleic acid sequence may be from 37-50 nucleotides. The first and second nucleic acid sequence may be separated by a third sequence of from 8-12 nucleotides. The hairpin structure may have a free energy less than −25 Kcal/mole as calculated by the Vienna algorithm with default parameters, as described in Hofacker et al., Monatshefte f. Chemie 125: 167-188 (1994), the contents of which are incorporated herein. The hairpin may comprise a terminal loop of 4-20, 8-12 or 10 nucleotides.

The nucleic acid of the present invention may also comprise a sequence of a pre-miRNA or a variant thereof. The pre-miRNA sequence may comprise from 45-90, 60-80 or 60-70 nucleotides. The sequence of the pre-miRNA may comprise a miRNA and a miRNA*. The pre-miRNA may also comprise a miRNA or miRNA* and the complement thereof, and variants thereof. The sequence of the pre-miRNA may also be that of a pri-miRNA excluding from 0-160 nucleotides from the 5' and 3' ends of the pri-miRNA. The pre-miRNA of the present invention may comprise the sequence of SEQ ID NOs: 1-6, or variants thereof.

The nucleic acid of the present invention may also comprise a sequence of a miRNA, miRNA* or a variant thereof. The miRNA sequence may comprise from 5-50, 13-33, 18-24 or 21-23 nucleotides. The sequence of the miRNA may be the first 13-33 nucleotides of the pre-miRNA. The sequence of the miRNA may be the last 13-33 nucleotides of the pre-miRNA. The sequence of the miRNA may comprise the sequence of SEQ ID NOs: 1-6, or variants thereof.

The nucleic acid of the invention may also comprise a sequence of an anti-miRNA that is capable of blocking the activity of a miRNA or miRNA*. The anti-miRNA may comprise a total of 5-100 or 10-60 nucleotides. The anti-miRNA may also comprise a total of at least 5, 6, 7, 8, 9, 10, 11, 12, 13, 14, 15, 16, 17, 18, 19, 20, 21, 22, 23, 24, 25 or 26 nucleotides. The sequence of the anti-miRNA may comprise (a) at least 5 nucleotides that are substantially identical to the 5' of a miRNA and at least 5-12 nucleotide that are substantially complimentary to the flanking regions of the target site from the 5' end of said miRNA, or (b) at least 5-12 nucleotides that are substantially identical to the 3' of a miRNA and at least 5 nucleotide that are substantially complimentary to the flanking region of the target site from the 3' end of said miRNA. The sequence of the anti-miRNA may comprise the compliment of a sequence of a miRNA.

The nucleic acid of the invention may also comprise a sequence of a target miRNA binding site, or a variant thereof. The target site sequence may comprise a total of 5-100 or 10-60 nucleotides. The target site sequence may comprise at least 5 nucleotides of the sequence of a target gene binding site.

The present invention also relates to a synthetic gene comprising a nucleic acid of the invention operably linked to a transcriptional and/or translational regulatory sequence. The synthetic gene may be capable of modifying the expression of a target gene with a binding site for the nucleic acid of the invention. Expression of the target gene may be modified in a cell, tissue or organ. The synthetic gene may be synthesized or derived from naturally-occurring genes by standard recombinant techniques. The synthetic gene may also comprise terminators at the 3'-end of the transcriptional unit of the synthetic gene sequence. The synthetic gene may also comprise a selectable marker.

The present invention also relates to a vector comprising any nucleic acid of the invention or a synthetic gene of the invention. The vector may be an expression vector. An expression vector may comprise additional elements. For example, the expression vector may have two replication systems allowing it to be maintained in two organisms, e.g., in mammalian or insect cells for expression and in a prokaryotic host for cloning and amplification. For integrating expression vectors, the expression vector may contain at least one sequence homologous to the host cell genome, and preferably two homologous sequences which flank the expression construct. The integrating vector may be directed to a specific locus in the host cell by selecting the appropriate homologous sequence for inclusion in the vector. The vector may also comprise a selectable marker gene to allow the selection of transformed host cells.

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrate into a host genome. One type of vector is a "plasmid", which refers to a linear or circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. The invention is also intended to include such other forms of expression vectors, such as viral vectors (e.g., replication defective retroviruses, adenoviruses and adeno-associated viruses), which serve equivalent functions. Additionally, some viral vectors are capable of targeting a particular cells type either specifically or non-specifically.

The present invention also relates to a host cell comprising an isolated nucleic acid or a vector of the invention. The cell may be a bacterial, fungal, plant, insect or animal cell. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. Additionally, host cells could be modulated once expressing PDX, and may either maintain or loose original characteristics.

A host cell can be any prokaryotic or eukaryotic cell. For example, any of the polypeptides or polynucleotide sequences of the present invention can be expressed in bacterial cells such as E. coli, insect cells, yeast or mammalian cells (such as Chinese hamster ovary cells (CHO) or COS cells). Alternatively, a host cell can be a premature mammalian cell, i.e., pluripotent stem cell. A host cell can also be derived from other human tissue. Other suitable host cells are known to those skilled in the art.

Vector can be introduced into prokaryotic or eukaryotic cells via conventional transformation, transduction, infection or transfection techniques. As used herein, the terms "transformation" "transduction", "infection" and "transfection" are intended to refer to a variety of art recognized techniques for introducing foreign nucleic acid (e.g., DNA) into a host cell, including calcium phosphate or calcium chloride co precipitation, DEAE dextran mediated transfection, lipofection, or electroporation. In addition transfection can be mediated by a transfection agent. By "transfection agent" is meant to include any compound that mediates incorporation of DNA in the host cell, e.g., liposome. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

Transfection may be "stable" (i.e. integration of the foreign DNA into the host genome) or "transient" (i.e., DNA is episomally expressed in the host cells).

The present invention also relates to a probe comprising a nucleic acid of the invention. Probes may be used for screening and diagnostic methods. The probe may be attached or immobilized to a solid substrate, such as a biochip.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids of the present invention. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

The probe may have a length of from 8 to 500, 10 to 100 or 20 to 60 nucleotides. The probe may also have a length of at least 8, 9, 10, 11, 12, 13, 14, 15, 16, 17, 18, 19, 20, 21, 22, 23, 24, 25, 26, 27, 28, 29, 30, 35, 40, 45, 50, 60, 70, 80, 90, 100, 120, 140, 160, 180, 200, 220, 240, 260, 280 or 300 nucleotides. The probe may further comprise a linker sequence of from 10-60 nucleotides.

The probe may comprise a nucleic acid of any one of SEQ ID NOs: 1-6, or variants thereof. The probe may comprise at least 8-22 contiguous nucleotides complementary to any one of SEQ ID NOs: 1-6.

The present invention also relates to a plurality of the probes. The plurality of probes may comprise at least one probe complementary to each SEQ ID NOs: 1-6, or variants thereof. The plurality of probes may comprise at least one probe having at least 8-22 contiguous nucleotides complementary to any one of SEQ ID NOs: 1-6.

The most commonly used method for discovering novel miRNAs is to search high-throughput sequencing reads for expression patterns indicative of miRNAs. Current algorithms designed for this purpose have several biases and flaws: (1) they are biased for highly expressed and/or easily sequenced miRNAs; (2) they are biased against miRNAs whose genes are located in low complexity regions of the genome; and (3) they have no functional emphasis so they provide little to no information that would be useful for a specific purpose such as finding biomarkers.

The present invention provides an innovative and powerful method of identifying novel disease-related miRNAs. The method comprises steps of a) searching in a deep sequencing database using a seed sequence of a known miRNA that is associated with at least one disease, wherein the seed sequence consists of at least 6 nucleotides; b) identifying a read sequence in the deep sequencing database, wherein 0 or 1 mismatch exists when the seed sequence is aligned against the first 12 non-adaptor nucleotides at the 5' end of the read sequence; c) searching human genome database using a fragment of the read sequence consisting of the seed sequence and 10-12 nucleotides of the read sequence extended from the 3' end of the seed sequence; d) identifying in the human genome database a target sequence, wherein the fragment of the read sequence 100% matches the target sequence; e) determining the presence of a hairpin in a query sequence, wherein the query sequence consists of the fragment of the read sequence and 50-100 nucleotides of the target sequence extended from both the 5' and 3' ends of the fragment of the read sequence; f) determining the position of the seed sequence relative to the terminal loop of the hairpin within the query sequence when the hairpin is present; and g) identifying a novel miRNA sequence, wherein the seed sequence is 20-35 nucleotides upstream or 0-10 nucleotides downstream of the terminal loop of the hairpin.

As used herein "a deep sequencing database" refers to the output from a high-throughput sequencing experiment. A collection of 15-40 nucleotide reads produced from one or more high-throughput sequencing experiments that represent whole or pieces of RNA transcripts in a biological sample.

As used herein "a seed sequence" refers to the first 6-10 nucleotides located at the 5' end of a miRNA that determines its target specificity. The seed sequence perfectly aligns with a complimentary sequence within the target mRNA, often located at multiple sites in the 3' UTR. Thus, multiple miRNA molecules with the same seed sequence can attack the same target mRNA. miRNAs with similar seeds are defined to be members of the same "seed family". An skilled artisan in this field can identify a seed sequence without undue experimentations. An exemplary seed sequence that can be used for the method of the present invention is the mir-122 seed (UGGAGUG, SEQ ID NO: 8).

As used herein "an adaptor" or "adaptor nucleotides" refers to a synthetic oligonucleotide that is added to each end of a RNA fragment during deep sequencing for the purpose of amplification of the RNA. Sometimes, the adaptor is left on the read sequence in deep sequencing database. Thus, non-adaptor nucleotides refer to nucleotides of a read sequence that are not adaptor nucleotides.

By "upstream", it means relatively closer to the 5' end of a nucleic acid. For example, the phrase "the seed sequence is 20-35 nucleotides upstream of the hairpin" means the seed sequence is located at the 5' end of the hairpin with 20-35 nucleotides between these two sequences.

By "downstream", it means relatively closer to the 3' end of a nucleic acid. For example, the phrase "the seed sequence is 0-10 nucleotides downstream of the hairpin" means the seed sequence is located at the 3' end of the hairpin with 0-10 nucleotides between these two sequences.

A skilled artisan can readily determine a hairpin and the terminal loop of the hairpin based on their knowledge or any software that is available.

Methods of Use

1. Methods

The compositions of the present invention are candidates for preventing, treating or alleviating at least one symptom of certain conditions and diseases, particularly conditions and diseases associated with chronic liver disease. These compositions include: an isolated nucleic acid, a probe, a plurality of probes, a vector or a cell of the present invention, and a pharmaceutical composition thereof.

The present invention also provides methods of treating or alleviating a symptom of a liver disease or an extrahepatic Hepatitis-linked disease. The method includes administering to a subject, a therapeutically effective amount of at least one composition of the present invention. Preferably, the at least one composition comprises at least one isolated nucleic acid of the present invention.

The present invention also provides methods of preventing at least one symptom of a liver disease. The method includes administering to a subject, a therapeutically effective amount of at least one composition of the present invention. Preferably, the at least one composition comprises at least one isolated nucleic acid of the present invention.

The present invention further provides uses of at least one compositions of the present invention for the preparation of a medicament useful for the treatment of a liver disease. Preferably, the at least one composition comprises at least one isolated nucleic acid of the present invention.

The present invention further provides uses of at least compositions of the present invention for the preparation of a medicament useful for the prevention of a liver disease. Preferably, the at least one composition comprises at least one isolated nucleic acid of the present invention.

In a preferred embodiment, the present invention provides methods of treating or alleviating a symptom of a liver disease selected from a group consisting of Hepatitis C, Hepatitis B, or hepatocellular carcinoma by administering to a subject, a therapeutically effective amount of a composition comprising a nucleic acid of any of SEQ ID NOs: 1-6.

The present invention also provides combination therapies for preventing, treating or alleviating at least one symptom of a liver disease in a subject. At least one or more agents can be used in combination with at least one composition of the present invention. The additional agents may be for example, but are not limited to, immune therapies (e.g., interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, antimuscarinics, anti-leukotrienes, inhibitors of cell adhesion (e.g., ICAM antagonists), anti-oxidants (e.g., N-acetylcysteine), cytokine agonists, cytokine antagonists, lung surfactants antimicrobial and anti-viral agents (e.g., ribavirin and amantidine), protease inhibitors, helicase inhibitors, antibody therapy (monoclonal and polyclonal), and/or miRNAs and variants (e.g., Miravisen).

The compositions according to the invention may also be used in combination with interferon alfa-2b, interferon alfa-2a, and interferon alfacon-1, L-deoxythymidine, adfovir, lamivudine, tenfovir, ribavirin, teleprevir, boceprevir, Sorafenib (Nexavar), a cytochrome P450 monoxygenase inhibitor (CYP inhibitor), and/or Miravisen. CYP inhibitors include, but are not limited to, ritonavir, ketoconazole, troleandomycin, 4-methyl pyrazole, cyclosporin, clomethiazole, cimetidine, itraconazole, fluconazole, miconazole, fluvoxamine, fluoxetine, nefazodone, sertraline, indinavir, nelfinavir, amprenavir, fosamprenavir, saquinavir, lopinavir, delavirdine, erythromycin, VX-944, and VX-497. Preferred CYP inhibitors include ritonavir, ketoconazole, troleandomycin, 4-methyl pyrazole, cyclosporin, and clomethiazole. Preferably, the additional agent is Miravirsen. The at least one additional agent can be administered to the subject prior to, concurrently, or after the administration of the composition of the present invention.

The present invention also relates to a method of diagnosing or predicting a risk of developing a liver disease in a subject. The method includes steps of obtaining a sample from the subject; measuring the level of a nucleic acid of the present invention and comparing the level of the nucleic acid of the present invention to a reference value. A difference (an increase or a decrease) in the level of the nucleic acid between the sample and the reference value indicates the presence or the risk of developing the liver disease in the tested subject.

"Risk" in the context of the present invention, relates to the probability that an event will occur over a specific time period and can mean a subject's "absolute" risk or "relative" risk. Absolute risk can be measured with reference to either actual observation post-measurement for the relevant time cohort, or with reference to index values developed from statistically valid historical cohorts that have been followed for the relevant time period. Relative risk refers to the ratio of absolute risks of a subject compared either to the absolute risks of low risk cohorts or an average population risk, which can vary by how clinical risk factors are assessed. Odds ratios, the proportion of positive events to negative events for a given test result, are also commonly used (odds are according to the formula p/(1-p) where p is the probability of event and (1- p) is the probability of no event) to no-conversion.

The present invention also provides a method of characterizing a liver disease in a subject. The method comprises steps of obtaining a sample from the subject, measuring the level of a nucleic acid of the present invention and comparing the level of the tested nucleic acid to a reference value. A similarity of the level of the nucleic acid between the sample and the reference value indicates a characteristic of the liver disease represented by the reference value in the tested subject.

Cytochrome P450 enzymes are a heme-containing family that play central roles in oxidative, peroxidative and reductive metabolism of numerous endogenous and exogenous compounds, including many pharmaceutical agents. Substances known to be metabolized by P450 enzymes include steroids, bile acids, fatty acids, prostaglandins, leukotrienes, biogenic amines, retinoids, lipid hydroperoxides, phytoalexins, pharmaceuticals, environmental chemicals and pollutants.

The CYP2C and CYP3A subfamilies are unique in that they are present in large amounts in human liver microsomes, and there are many forms in each subfamily. The most important members of the CYP3A subfamily are CYP3A4, CYP3A5 and CYP3A7. The CYP3A subclass catalyzes a remarkable number of oxidation reactions of clinically important drugs such as quinidine, warfarin, erythromycin, cyclosporin A, midazolam, lidocain, nifedipine, and dapsone. Current estimates are that more than 60% of clinically used drugs are metabolized by the CYP3A4 enzyme, including such major drug classes as calcium channel blockers, immunosuppressors, macrolide antibiotics and anticancer drugs, see Brian et al. (1990) Biochemistry 29:11280-11292. CYP3A4 has been associated with many important diseases, particularly cancer and liver diseases.

Accordingly, the present invention provides a method of diagnosing or predicting a risk of developing a CYP3A4 associated disorder in a subject. The method includes steps of obtaining a sample from the subject; measuring the level of a nucleic acid of the present invention and comparing the level of the nucleic acid of the present invention to a reference value. A difference (an increase or a decrease) in the level of nucleic acid of the present invention between the sample and the reference value indicates the presence or the risk of developing the CYP3A4 associated disorder in the subject. A CYP3A4 associated disorder may be a liver disease. Alternatively, a CYP3A4 associated disorder is cancer. Preferably, the nucleic acid measured comprises SEQ ID NO: 1 or 2.

Since the rates of metabolism of drugs, toxins, etc. can depend on the amounts and kinds of P450s expressed in a tissue, variation in biological response may be determined by the profile of expression of P450s in each person.

Figure 7:
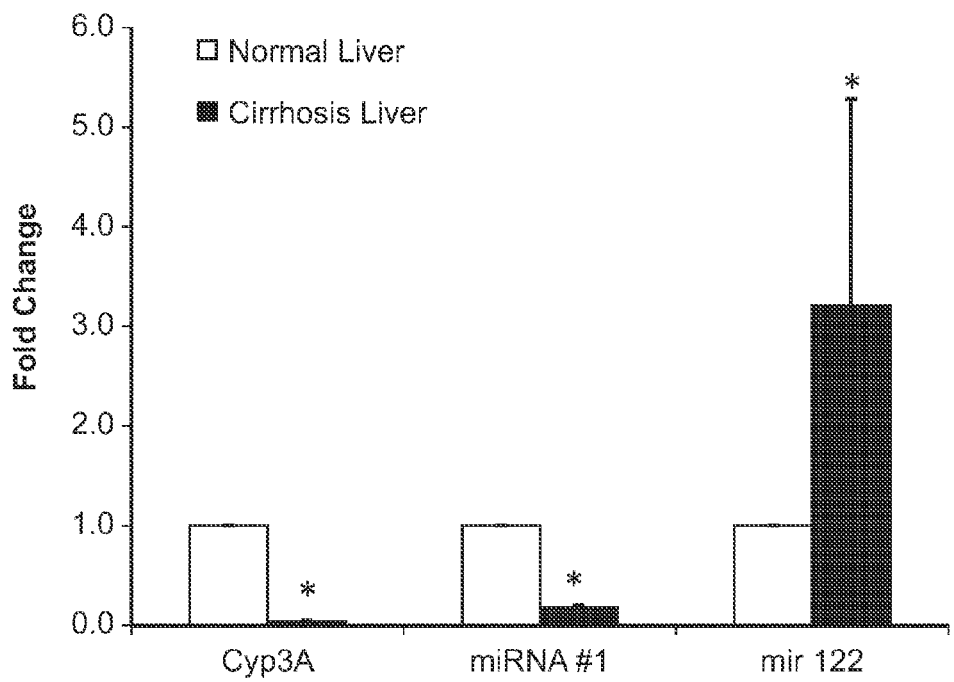
FIG. 7 is a graph demonstrating similar expression profile of miRNA #1 and CYP3A4 in normal and cirrhosis liver.
Figure 8:
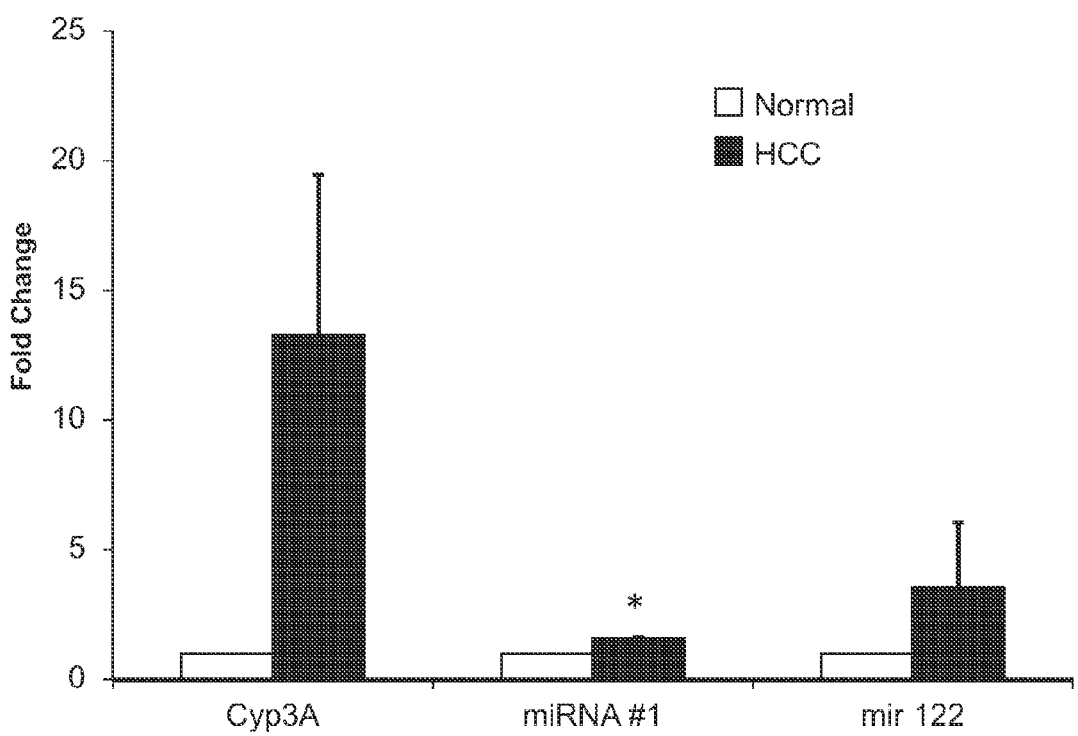
FIG. 8 is a graph demonstrating similar expression profile of miRNA #1 and CYP3A4 in normal and HCC liver.
Figure 9:
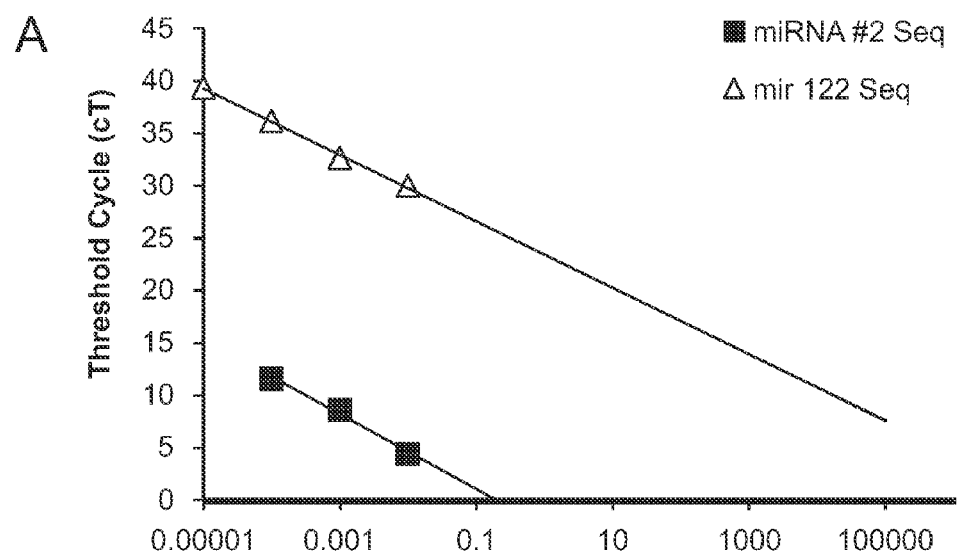
FIGS. 9A and 9B are a panel of graphs demonstrating the specificity of primers for miRNA #2.
Figure 9:
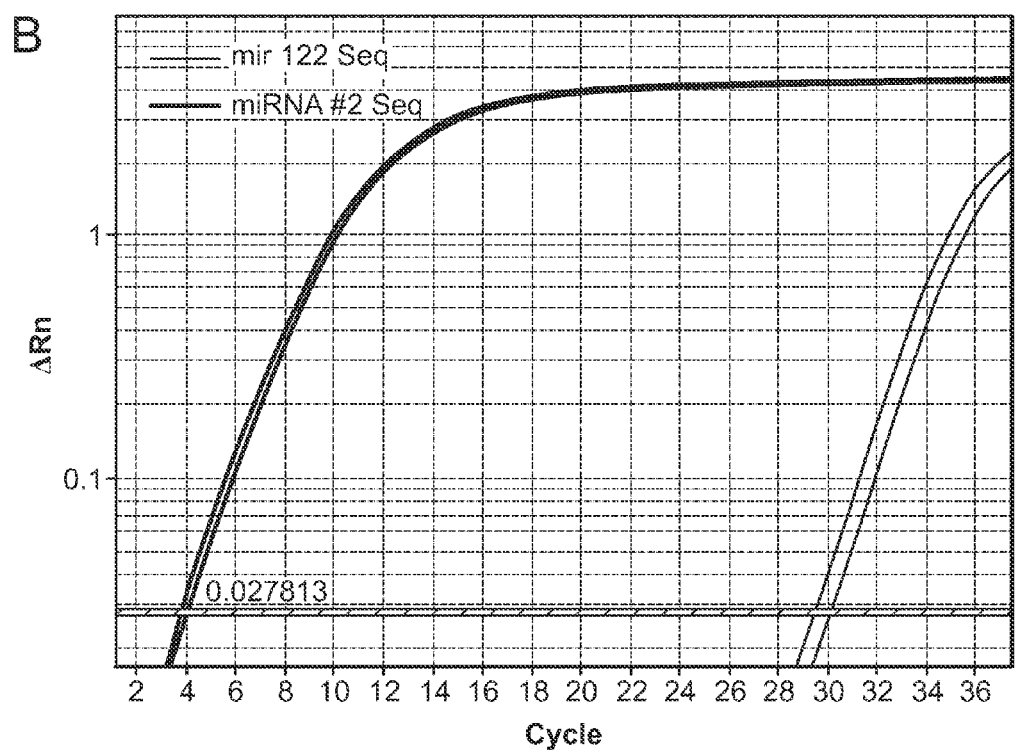

Accordingly, the present invention provides a simple, reliable and accurate method to determine the level (or expression profile) of CYP3A4 in a sample, based upon the surprising discovery that the level (or expression profile) of a nucleic acid comprising SEQ ID NO: 1 or 2 is highly correlated with the level (or expression profile) of CYP3A4 in the sample (see, e.g., FIG. 7). Compared to the traditional methods that involve ingesting a substrate for CYP3 enzymes and then measuring the amount of metabolites of the substrate in a blood sample, the method of the present invention is much more efficient, reliable and accurate.

The present invention provides a method of determining CYP3A4 level (or expression profile) in a subject. The method comprises the steps of obtaining a sample from the subject; measuring the level of a nucleic acid comprising SEQ ID NO: 1 or 2 in the sample and determining CYP3A4 level (or expression profile) in the sample based on the level of the nucleic acid measured in the sample. The level of the nucleic acid measured in the sample indicates a similar level (or expression profile) of CYP3A44 in the sample. In other words, a high level of the nucleic acid measured in the sample compared to a reference value indicates a high level of CYP3A4 in the same sample; and a low level of the nucleic acid measured in the sample compared to a reference value indicates a low level of CYP3A4 in the same sample The present invention also provides a method of determining a dosing regimen of a drug in a subject. The method comprises the steps of obtaining a sample from the subject; measuring the level of a nucleic acid comprising SEQ ID NO: 1 or 2 in the sample and comparing the level of the nucleic acid in the sample to a reference value. An increase in the level of the nucleic acid in the sample compared to the reference value indicates that a higher dosing regimen than average is required for the subject. Preferably, the drug tested is a chemotherapeutic drug.

The measuring step may be carried out prior to or after the administration of the tested drug.

The present invention further provides a method of determining toxicity of a drug in a subject. The method comprises steps of obtaining a first sample from the subject; measuring a first level of a nucleic acid comprising SEQ ID NO: 1 or 2 in the first sample; administering the drug to the subject; obtaining a second sample from the subject measuring a second level of a nucleic acid comprising SEQ ID NO: 1 or 2 in the second sample; and comparing the second level of the nucleic acid in the second sample to the first level of the nucleic acid in the first sample. An increase in the level of the nucleic acid in the second sample compared to the first sample indicates the tested drug is toxic.

To measure the amount/level of a particular nucleic acid of the present invention, any assay known in the art for the detection of nucleic acids may be used in the invention. Examples include, but are not limited to, reverse transcription and amplification assays (such as PCR, ligation RT-PCR or quantitative RT-PCT), hybridization assays, Northern blotting, dot blotting, in situ hybridization, gel electrophoresis, capillary electrophoresis, and column chromatography. Assays can be performed directly on biological samples or on nucleic acids isolated from the samples. It is routine practice in the relevant art to carry out these assays.

An increase in the level of a particular nucleic acid of the present invention in any methods described herein means an increase in the level of the tested nucleic acid by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 1000%, 1500%, or more compared to a reference value or the level of this nucleic acid measured in a different sample.

A decrease in the level of a particular nucleic acid of the present invention in any methods described herein means a decrease in the level of the tested nucleic acid by at least 5%, 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%,1000%, 1500%, or more compared to a reference value or the level of this nucleic acid measured in a different sample.

A similarity means the amount/level of a particular nucleic acid of the present invention derived from different samples is identical or less than 5%, 4%, 3%, 2%, or 1% in difference.

In a preferred embodiment, the liver disease of the present invention is a chronic liver disease. In a more preferred embodiment, the liver disease of the present invention is selected from the group consisting of Hepatitis C, Hepatitis B, hepatocellular carcinoma, metastatic liver cancer, alcohol-induced liver disease, non-alcohol-induced liver disease, cirrhosis, diabetes-related liver damage, and Alcoholic Fatty Acid Liver Disease (AFLD). More preferably, the liver disease of the present invention is Hepatitis C, Hepatitis B, or hepatocellular carcinoma.

In a preferred embodiment, the nucleic acid measured in any methods of the present invention comprises any one of SEQ ID NOs: 1-6.

2. Definitions

As used herein, a "subject" includes a mammal. The mammal can be e.g., a human or appropriate non-human mammal, such as primate, mouse, rat, dog, cat, cow, horse, goat, camel, sheep or a pig. The subject can also be a bird or fowl. In one embodiment, the mammal is a human. A subject can be male or female.

A subject can include those who have not been previously diagnosed as having an extrahepatic Hepatitis-linked disease, a liver disease, a condition related to liver disease or a CYP3A4-associated disorder. Alternatively, a subject can also include those who have already been diagnosed as having an extrahepatic Hepatitis-linked disease, a liver disease, a condition related to a liver disease or a CYP3A4-associated disorder.

Optionally, the subject has been previously treated with a surgical procedure or other therapeutic treatments for removing an extrahepatic Hepatitis-linked disease, a liver disease, a condition related to liver disease or a CYP3A4-associated disorder. A subject can be one who had a liver disease, a condition related to liver disease or a CYP3A4-associated disorder.

A subject can also include those who are suffering from, or at risk of developing an extrahepatic Hepatitis-linked disease, a liver disease, a condition related to liver disease or a CYP3A4-associated disorder, such as those who exhibit known risk factors for a liver disease, a condition related to liver disease or a CYP3A4-associated disorder. Known risk factors include, but are not limited to, alcohol consumption, unprotected sexual intercourse, sharing unsterilized drug injecting equipment, using non-sterilized equipment for tattoos or body piercing, genetic inheritance, chemical exposure (such as anabolic steroids, viny chloride and carbon tetrachloride), acetaminophen (Tylenol) overdose, and medications that irritate the blood vessels causing narrowing or formation of blood clots (such as birth control pills).

As used herein, "treating" or "treat" describes the management and care of a patient for the purpose of combating a disease, condition, or disorder and includes the administration of a composition of the present invention, or a pharmaceutical composition thereof, to alleviate the symptoms or complications of a disease, condition or disorder, or to eliminate the disease, condition or disorder (such as a chronic liver disease). The term "treat" can also include treatment of a cell in vitro or an animal model.

As used herein, the term "alleviate" is meant to describe a process by which the severity of a sign or symptom of a disorder is decreased. Importantly, a sign or symptom can be alleviated without being eliminated. In a preferred embodiment, the administration of the compositions of the invention leads to the elimination of a sign or symptom, however, elimination is not required. Effective dosages are expected to decrease the severity of a sign or symptom. For instance, a sign or symptom of a disorder such as liver cancer, which can occur in multiple locations, is alleviated if the severity of the cancer is decreased within at least one of multiple locations.

As used herein, "preventing" or "prevent" describes reducing or eliminating the onset of the symptoms or complications (such as the destruction of liver tissue) of the liver disease.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is hepatitis B, hepatitis C, or liver cancer. In another aspect, the disease or condition to be treated is a chronic liver disease.

A "reference or baseline level/value" as used herein can be used interchangeably and is meant to be relative to a number or value derived from population studies, including without limitation, such subjects having similar age range, disease status (e.g., stage), subjects in the same or similar ethnic group, or relative to the starting sample of a subject undergoing treatment for a liver disease. Such reference values can be derived from statistical analyses and/or risk prediction data of populations obtained from mathematical algorithms and computed indices of a liver disease. Reference indices can also be constructed and used using algorithms and other methods of statistical and structural classification.

In one embodiment of the present invention, the reference or baseline value is the amount/level of a nucleic acid of the present invention in a control sample derived from one or more healthy subjects or subjects who have not been diagnosed with any extrahepatic Hepatitis-linked disease, any liver disease or any CYP3A4 associated disorders. For example, a difference (an increase or a decrease) in the amount/level of the nucleic acid measured in the subject's sample from the reference value indicates the presence or the risk of developing an extrahepatic Hepatitis-linked disease, a liver disease or a CYP3A4 associated disorder in the tested subject. Preferably, the measured nucleic acid comprises a sequence of any one of SEQ ID NOs: 1-6. A liver disease may be selected from a group consisting of Hepatitis C, Hepatitis B, hepatocellular carcinoma, metastatic liver cancer, alcohol-induced liver disease, non-alcohol-induced liver disease, cirrhosis, diabetes-related liver damage, and Alcoholic Fatty Acid Liver Disease (AFLD). In a preferred embodiment, the liver disease is Hepatitis C, Hepatitis B, or hepatocellular carcinoma. A CYP3A4 associated disorder may be a liver disease or cancer. In a preferred embodiment, CYP3A4 associated disorder is Hepatitis C, Hepatitis B, or hepatocellular carcinoma.

In another embodiment of the present invention, the reference or baseline value is the amount/level of a nucleic acid of the present invention in a control sample derived from one or more subjects who have been diagnosed with a specific liver disease at a specific stage. A similarity between the amount/level of the nucleic acid measured in the tested subject's sample and the reference value can indicate the characteristic of the liver disease represented by the reference value. For example, the reference or baseline value is the amount of a nucleic acid of the present invention in a control sample derived from one or more subjects who have been diagnosed with a specific class of cirrhosis. The severity of cirrhosis is commonly classified with the Child-Pugh score. This score uses bilirubin, albumin, INR, presence and severity of ascites and encephalopathy to classify patients in class A, B or C; class A has a favorable prognosis, while class C is at high risk of death. Thus, a similarity between the amount/level of the nucleic acid measured in the tested subject's sample and the reference value derived from one or more subjects who have been diagnosed with a specific class of cirrhosis indicates the characteristic of this class of cirrhosis in the tested subject.

In another embodiment of the present invention, the reference or baseline value is the amount/level of a nucleic acid of the present invention in a control sample derived from one or more subjects who have a normal metabolism level for a tested drug. An increase in the level of a nucleic acid comprising SEQ ID NO: 1 or 2 in the tested subject's sample compared to the reference value can indicate a higher dosing regimen than average required for the tested subject.

An average dosing regimen used in accordance with the invention varies depending on the agent, the age, weight, and clinical condition of the recipient patient, and the experience and judgment of the clinician or practitioner administering the therapy, among other factors affecting the selected dosage. An ordinarily skilled physician or veterinarian can readily determine and prescribe the average dosing regimen of the drug required to prevent, counter, or arrest the progress of the condition.

An ordinarily skilled physician or veterinarian can also readily determine and/or establish a reference value utilizing routine procedures.

By "sample" it means any biological sample derived from the subject, includes but is not limited to, cells, tissues samples, and body fluids (including, but not limited to, mucus, blood, plasma, serum, urine, saliva, and semen). A sample can be obtained by physicians utilizing routine procedures. Alternatively, a sample can be provided by the subject.

Pharmaceutical Composition

The present invention also provides pharmaceutical compositions comprising an isolated nucleic acid, a probe, a plurality of probes, a vector, or a cell line of the present invention, or any combination thereof, and optionally in combination with at least one pharmaceutically acceptable excipient or carrier.

A "pharmaceutical composition" is a formulation containing a composition (i.e., an isolated nucleic acid, a probe, a plurality of probes, a vector, or a cell line of the present invention, or any combination thereof) of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed nucleic acid sequences or variants thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a composition of this invention include powders, sprays, ointments, pastes, creams, lotions, gels, solutions, patches and inhalants. In one embodiment, the active composition is mixed under sterile conditions with a pharmaceutically acceptable carrier, and with any preservatives, buffers, or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A composition (e.g., an isolated nucleic acid, a probe, a plurality of probes, a vector or a cell line) or pharmaceutical composition of the invention can be administered to a subject in many of the well-known methods currently used for treatment of liver diseases. For example, for treatment of HCC, a composition of the invention may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., chronic liver disease, cirrhosis, liver cancer, and the like) and the health of the patient should preferably be closely monitored.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic selected for administration. Therapeutically effective amounts for a given situation can be determined by routine experimentation that is within the skill and judgment of the clinician. In a preferred aspect, the disease or condition to be treated is hepatitis B, hepatitis C, or liver cancer. In another aspect, the disease or condition to be treated is a chronic liver disease.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug interaction(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL.™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compositions can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer or other symptoms of the liver disease that can be treated by the compositions of the instant invention. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

The dosage regimen utilizing the compositions is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Techniques for formulation and administration of the disclosed compounds of the invention can be found in Remington: the Science and Practice of Pharmacy, $19^{th}$ edition, Mack Publishing Co., Easton, Pa. (1995). In an embodiment, the compositions described herein, and the pharmaceutically acceptable salts thereof, are used in pharmaceutical preparations in combination with a pharmaceutically acceptable carrier or diluent. Suitable pharmaceutically acceptable carriers include inert solid fillers or diluents and sterile aqueous or organic solutions. The compositions will be present in such pharmaceutical compositions in amounts sufficient to provide the desired dosage amount in the range described herein during and for a reasonable period after treatment.

Kits

A composition of the present invention may, if desired, be presented in a kit (e.g., a pack or dispenser device) which may contain one or more unit dosage forms containing the composition, for example an isolated nucleic acid, a probe, a plurality of probes, a pharmaceutical composition, a vector, or a cell of the present invention, or any combination thereof. The pack may for example comprise metal or plastic foil, such as a blister pack. The pack or dispenser device may be accompanied by instructions for administration. Compositions comprising a composition of the invention formulated in a compatible pharmaceutical carrier may also be prepared, placed in an appropriate container, and labeled for treatment of an indicated condition. Instructions for use may also be provided.

The kits may also include at least one detection reagent that detects the presence of an isolated nucleic acid of the present invention. For example, the kit may include probes, aptamers or oligonucleotide sequences. The kit may contain in separate containers an aptamer or a probe, control formulations (positive and/or negative), and/or a detectable label such as fluorescein, green fluorescent protein, rhodamine, cyanine dyes, Alexa dyes, luciferase, radiolabels, among others.

Instructions (e.g., written, tape, VCR, CD-ROM, etc.) for carrying out the assay may be included in the kit. The assay may for example be in the form of PCR, Western Blot analysis, Immunohistochemistry (IHC), immunofluorescence (IF), sequencing and Mass spectrometry (MS) as known in the art.

EXAMPLES

Example 1

General Methods

Phenol: Chloroform RNA Extration
1. Wash confluent cells (70%) twice with 15 ml of warmed PBS.
2. Lyse the cells by addition of 3 ml of TRIzol reagent and incubate on ice for 10 min.
3. Collect the cell lysates using a cell scraper into a microcentrifuge tube.

4. Add 0.6 ml of chloroform, shake vigorously by hand and centrifuge at 4° C. for 15 min at 12,000×g.
5. Remove the RNA containing aqueous phase and place in a separate container.
6. Add 1.5 ml of isopropyl alcohol, incubate on ice for 10 min, and centrifuge at 4° C. for 10 min at 12,000×g.
7. Remove the supernantant and discard.
8. Add 1 ml of 80% ethanol and centrifuge at 4° C. for 5 min at 7,500×g.
9. Remove supernatant and air dry the samples for 10 min.
10. Resuspend in 20 µl-100 µl of DEPC-treated water ar 55-60C for 10-15 min.

Northern Blotting
Electrophoresis
1. Assemble the Invitrogen electrophoresis apparatus with fresh novex electrophoresis gel according to manufacturers' directions. Remove the comb.
2. Pre-run the gel at 200V for 60 min at room temperature.
3. Prepare the sample: combine equal volumes of RNA (concentration may vary) and gel loading buffer II, denature the samples by heating to 95° C. for 5 min and then cool on ice.
4. Prepare the markers as follows: add 1 µl of low range ssRNA ladder to 20 µl of microRNA marker, denature the marker mix by heating to 95° C. for 5 min and cool on ice.
5. Wash the wells of the gel thoroughly to remove residual urea, which would interfere with electrophoretic separation.
6. Load the samples into each well of the electrophoresis gel.
7. Run the gel at 200V for approximately 50 min at room temperature or until the yellow dye of the marker reaches the bottom of the gel.
8. Remove the gel from the cassette, taking care not to rip it.
9. Incubate the gel in 1×TBE with 200 µg of ethidium bromide for 10 min.
10. Image the gel on the BioRad UV transilluminator. Avoid long UV exposure which would bind the RNA to the gel and reduce the amount of material transferred to a nylon membrane in subsequent steps.

Transfer
11. Incubate the transfer pads, 3 MM Whatman filter papers and nylon membrane in 1×TBE for 5 min.
12. Assemble the transfer sandwich as follows: transfer pad, 3×3 MM Whatman filter papers, gel, nylon membrane, 3×3 MM Whatman filter paper, 3× transfer pad, 3×3 MM Whatman filter papers, gel, nylon membrane, 3×3 MM Whatman filter paper, transfer pad. Remove air bubbles by rolling a conical tube over the sandwich. Place the sandwich in the BioRad SemiDry Transfer Box. Transfer at 16V for 50 min at 4° C.
13. Disassemble the transfer cassette, discard all but two 3 MM Whatman filter papers, and discard the gel as ethidium bromide contaminated waste.

Immobilization
14. Place the nylon membrane (RNA-side up) on one moist 3 MM Whatman filter paper and UV crosslink at 120,000 microjoules/cm$^2$ to covalently link RNA to nylon membrane.
15. Dry the membranes between two papers of 3 MM Whatman filter paper at 80° C. for approximately 30 min.

Hybridization
16. While drying the membranes warm the ULTRAhyb hybridization buffer to 65° C., then cool to hybridization temperature, which may vary by the target probe and stringency of the experiment (higher temp greater specificity of probe/target interactions).
17. Once dried using tweezers insert the dried membranes into 50 ml conical tubes.
18. Add 5 ml of the warmed ULTRAhyb hybridization buffer to each conical tube and pre-hybridize for 30 min at selected temperature.
19. Add the probe (concentration may vary; consult SOP: Probe Preparation) to each of the conical tubes and incubate overnight.

Detection
20. Discard the hydridization buffer. Wash the membrane twice with 15 ml of 2× SSC supplemented with 0.1% (wt/vol) SDS at selected temperature for 15 min (low stringency buffer) to remove nonspecifically bound probe.
21. Wash the membrane twice with 0.1×SSC supplemented with 0.1% (wt/vol) SDS at selected temperature for 15 min (high stringency buffer)
22. Wash the membrane once with 15 ml of 1×SSC for 10 min at 25° C. to remove SDS that otherwise would interfere with antibody binding in subsequent steps.
23. Incubate the membrane at 25° C. for 3hrs in 15 ml of the Roche blocking buffer diluted according to manufacturers' instructions (10× blocking buffer was diluted to 1× with 1× Roche washing buffer).
24. Add 1 µl of anti-digoxigenin antibody conjugated to alkaline phosphatase to the blocking buffer in which the membranes are incubated, yielding ratio of 1:15,000 and incubate at 25° C. for 30 min.
25. Wash membrane thrice at 25° C. for 15 min with 15 ml of Roche wash buffer-diluted according to manufacturers' instructions (10× washing buffer was diluted to lx with distilled water)- to remove the unbound anti-digoxigenin antibody.
26. Remove the membranes from 50 ml conical tubes with tweezers and incubate in a tray at 25° C. for 5 min in approximately 15 ml of Roche developing buffer diluted according to manufacturers' instructions (10× developing buffer was diluted to lx with distilled water).
27. Pippette approximately 200 µl of CSPD diluted 1:100 in Roche development buffer onto a sheet protector and place the membrane (RNA side down) on the CSPD solution. The enzymatic dephosphorylation of dioxetane, CSPD, by alkaline phosphatase, conjugated to the anti-dioxigenin antibody, results in emission at 477 nm.
28. Expose the membrane for 5-120 min to detect the signal.

RNA Isolation from Human Plasma
1. Thaw blood plasma (if frozen) on ice.
2. Combine 25 µl blood plasma with 250 µl of 2× denaturing solution.
3. Add 500 µl acid-phenol-chloroform solution, vortex for 30-60 sec and centrifuge for 5 min at maximum speed (≥10,000 ×g) at room temperature to separate the mixture into aqueous and organic phases.
4. Remove the aqueous phase without disturbing the interphase and transfer it to a new tube.
5. Add ⅓ volume of 100% ethanol to the aqueous phase and mix thoroughly.
6. Place a filter cartridge into one of the collection tubes supplied by the manufacturer and add the lysate/ethanol mixture, up to 700 µl, onto the filter cartridge. Centrifuge for ~30 sec or until the mixture has passed through the filter. Collect the filtrate.

7. Add ⅔ volume 100% ethanol to the filtrate, and mix thoroughly.
8. Pass the filtrate/ethanol mixture through a second filter cartridge, and discard the flow-through. 9. Add 700 µl miRNA Wash Solution 1 (working solution mixed with ethanol) to the filter cartridge and centrifuge for ~15 sec. Discard the flow-through from the collection tube.
10. Add 500 µL Wash Solution ⅔ (working solution mixed with ethanol) to the filter cartridge and centrifuge for ~15 sec. Discard the flow-through from the collection tube.
11. Repeat with a second 500µL of Wash Solution ⅔.
12. After discarding the flow-through from the last wash, replace the filter cartridge in the same collection tube and centrifuge the assembly for 1 min to remove residual fluid from the filter.
13. Transfer the filter cartridge into a fresh collection tube. Apply 100 µl of nuclease-free water to the center of the filter, and close the cap. Centrifuge for ~30 sec to recover the RNA.
14. Collect the eluate (which contains the RNA) and store it at −20° C. or −80C.

RNA Extraction From Urine
1. Centrifuge collected urine sample at 12000×g for 15 min at room temperature.
2. Combined 0.3 ml of supernatant with 1 ml of TRIzol reagent and incubate on ice for 10 min. (Keep in mind urine contains approximately ¼ of miRNAs of blood plasma)
3. Add 0.2 ml of chloroform, shake vigorously by hand and centrifuge at 4° C. for 15 min at 12,000×g.
4. Remove the RNA containing aqueous phase and place in a separate container.
5. Add 0.5 ml of isopropyl alcohol, incubate on ice for 10 min, and centrifuge at 4° C. for 10 min at 12,000×g.
6. Remove the supernatant and discard.
7. Add 1 ml of 80% ethanol and centrifuge at 4° C. for 5 min at 7,500×g.
8. Remove supernatant and air dry the samples for 10 min.
9. Re-suspend in 100 µl of DEPC-treated water at 55-60° C. for 10-15 min.

Example 2

YmirSCAN

Figure 18:
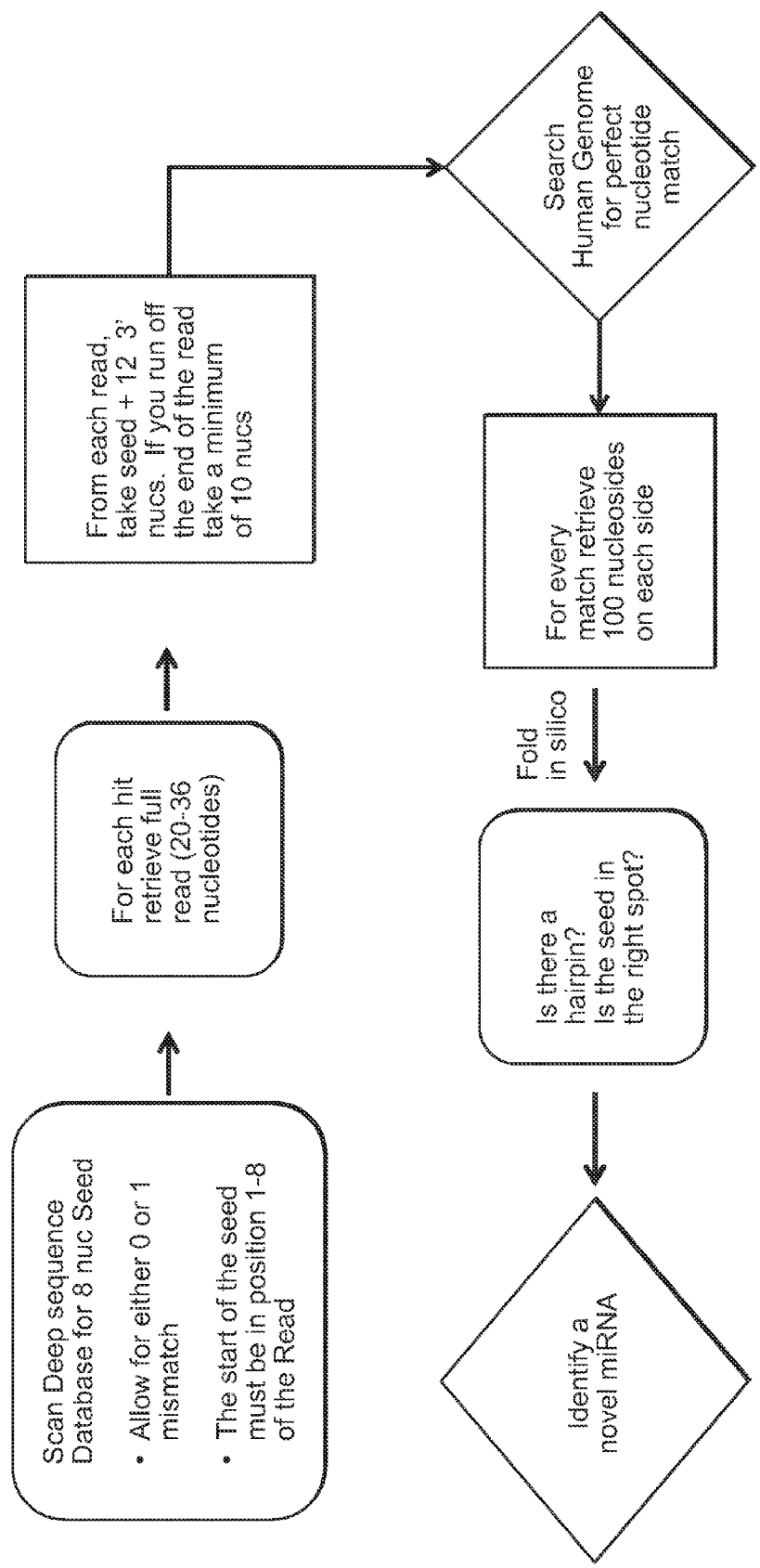
FIG. 18 is a graph showing a simplified scheme of YmirSCAN.

The most commonly used method for discovering novel miRNAs is to search high-throughput sequencing reads for expression patterns indicative of miRNAs. Current algorithms designed for this purpose have several biases and flaws: 1) they are biased for highly expressed and/or easily sequenced miRNAs; 2) they are biased against miRNAs whose genes are located in low complexity regions of the genome; and 3) they have no functional bias whatsoever so provide little to no information that would be useful for a specific purpose such as finding biomarkers. The present invention provides an innovative method (YmirSCAN) that addresses these flaws. This method hunts for novel miRNAs that are members of known miRNA seed families. YmirSCAN 1) systematically searches publicly available deep sequencing databases for sequenced reads that contain seed sequences at the appropriate position, 2) maps these reads to the human genome, 3) assesses the likelihood the read represents a microRNA, then 4) ranks potential micro-RNA candidates in an easily interpretable spreadsheet (see FIG. 18). No approach like this has been used to find novel miRNAs.

Example 3

Characterization of Novel miRNAs

Several publically available high throughput sequencing databases for a total of ~33 million reads from liver, liver cancer cell lines and some non-liver sources were downloaded. Three YmirSCAN runs with slightly different starting parameters using the mir-122 seed (UGGAGUG; SEQ ID NO: 8) were executed. YmirSCAN found mir-122 (positive control) and 127 novel candidate miRNAs. Of these, 7 were chosen for laboratory verification. 5 have been verified by PCR and/or Northern Blot as newly discovered miRNAs.

Figure 1:
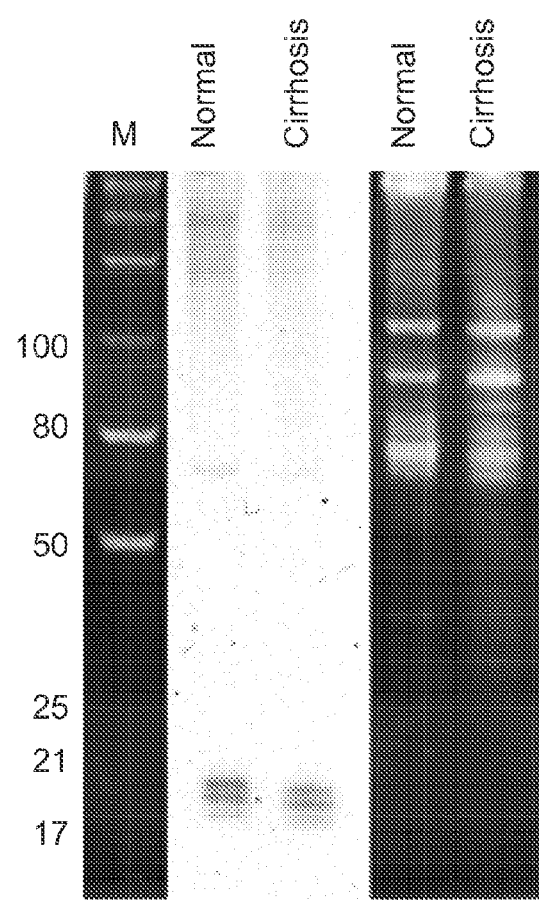
FIG. 1 an image of Northern blot showing detection of miRNA #1 in normal and cirrhosis samples.
Figure 2:
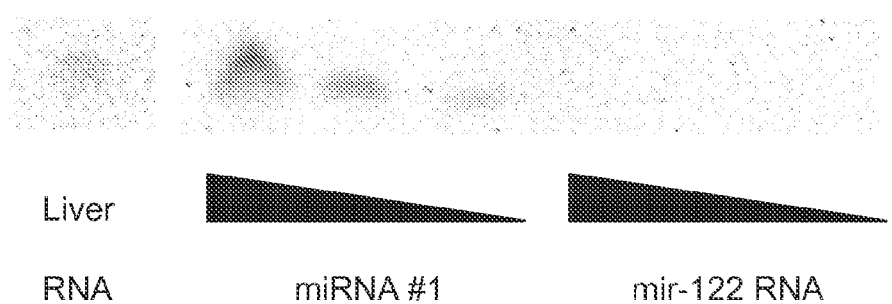
FIG. 2 is an image of Northern blot showing the specificity of probes for miRNA #1.
Figure 3:
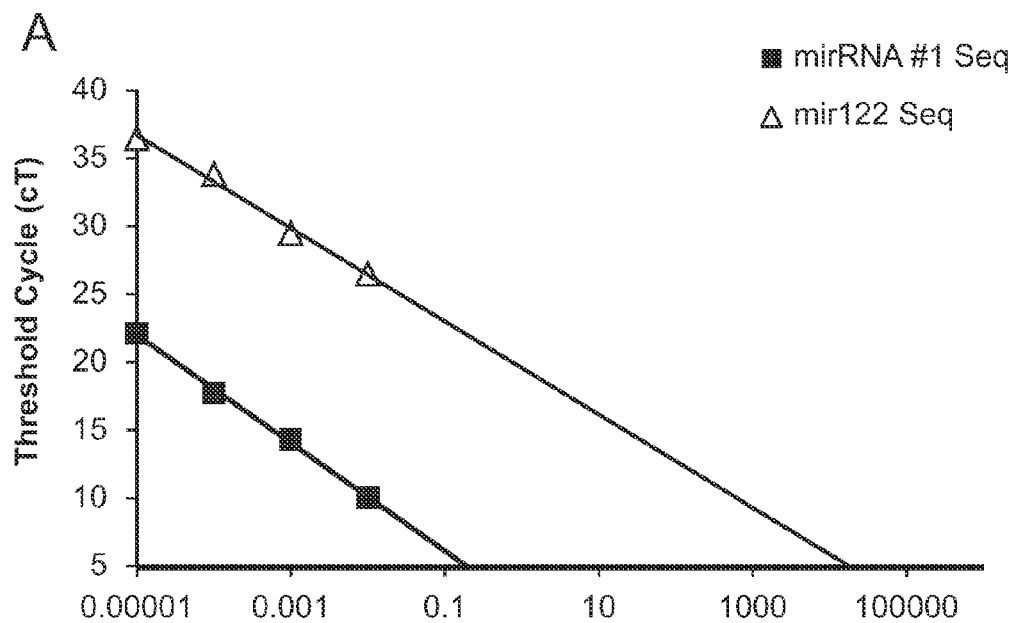
FIGS. 3A and 3B are a panel of graphs demonstrating the specificity of primers for miRNA #1.
Figure 3:
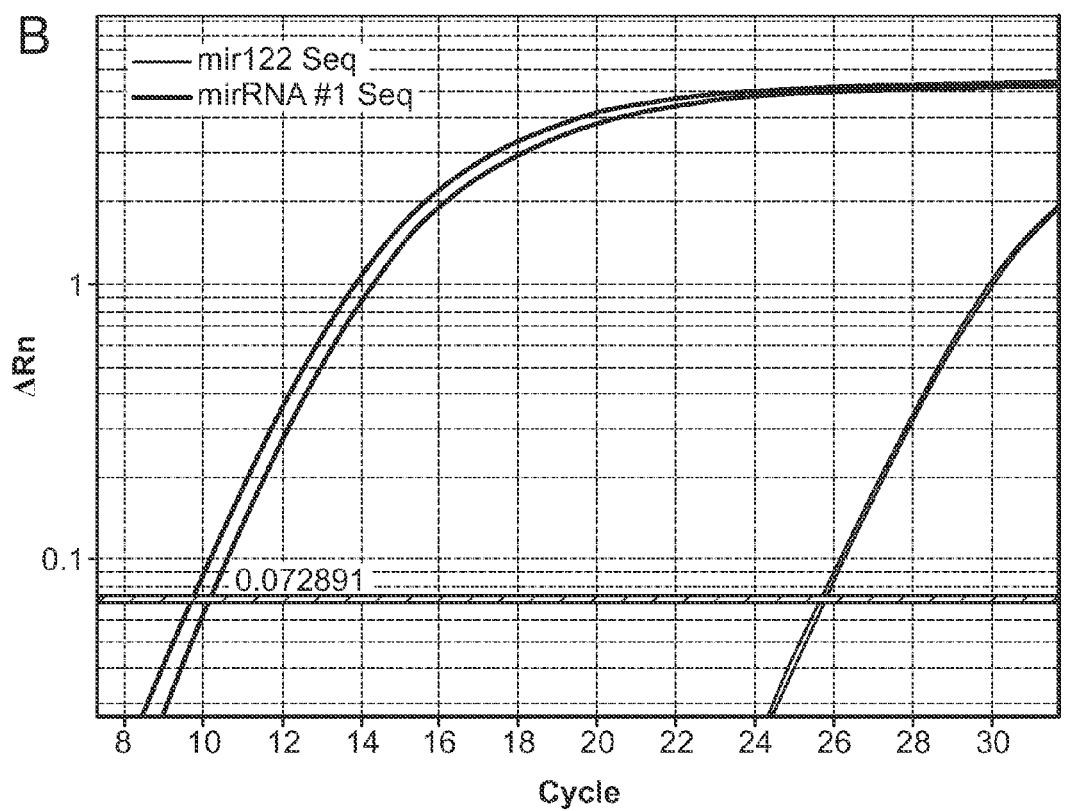
Figure 12:
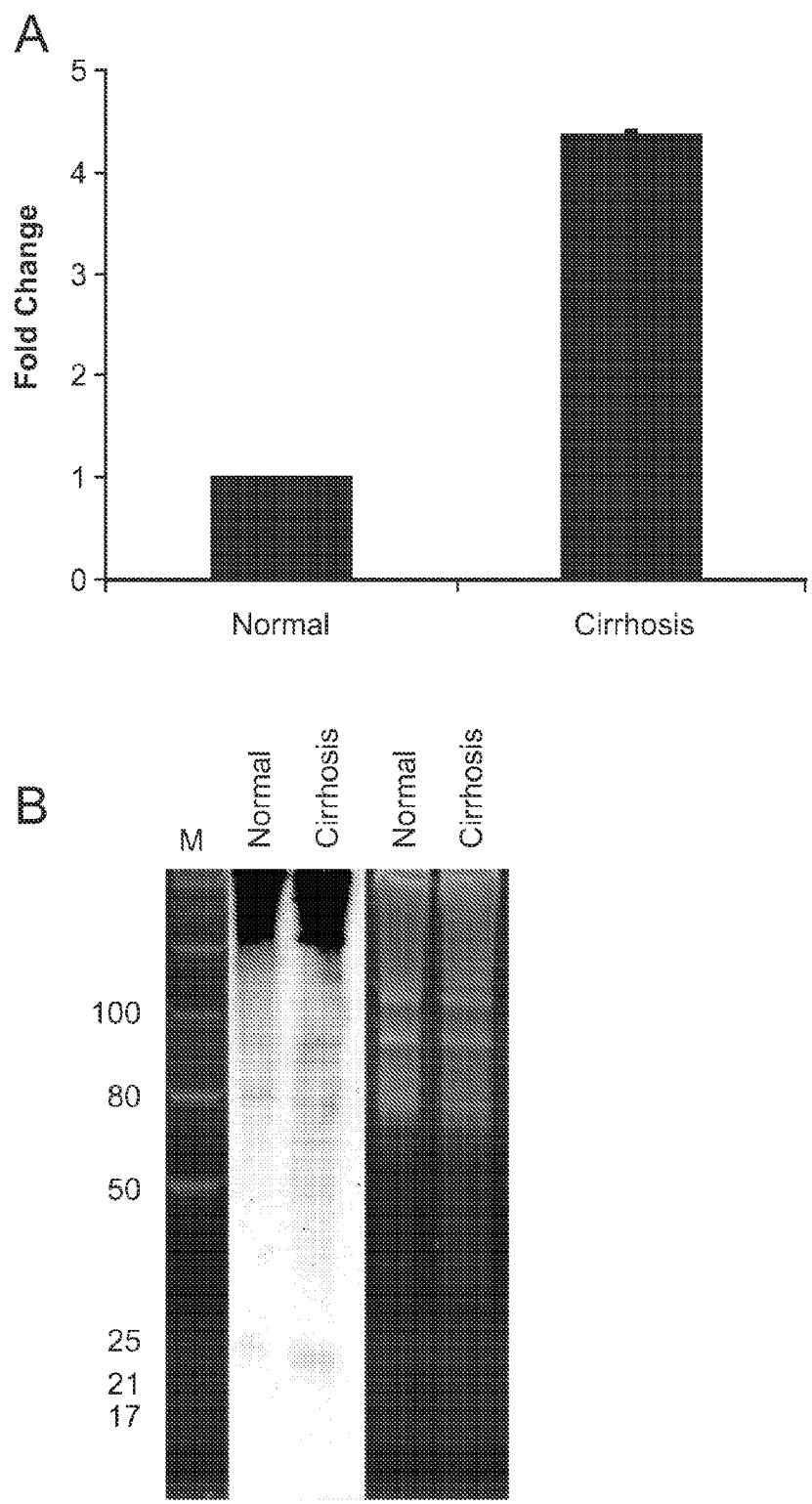
FIGS. 12A and 12B are a panel of graphs showing expression of miRNA #3 in normal and cirrhotic liver tissue by Northern blot (B) and quantitative fold change (A).
Figure 13:
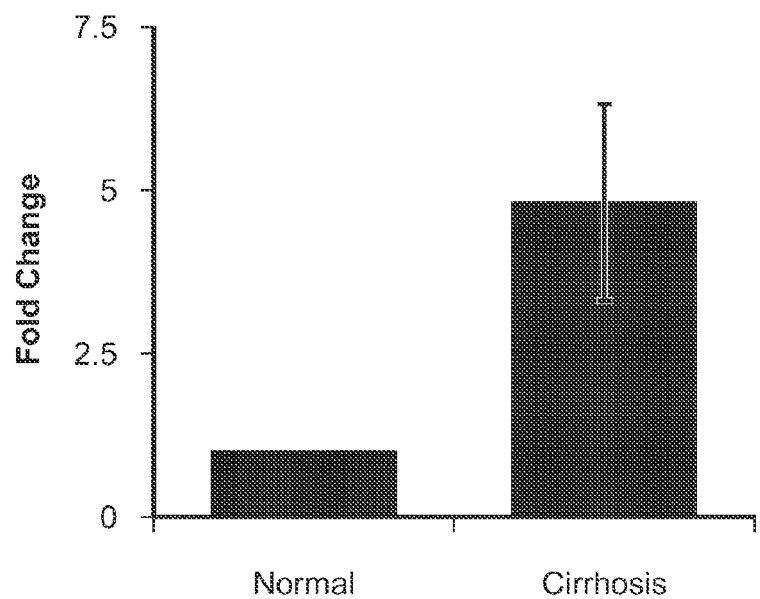
FIGS. 13A and 13B are a panel of graphs demonstrating detection of miRNA #3 by ligation RT-PCR in normal and cirrhotic liver.
Figure 13:
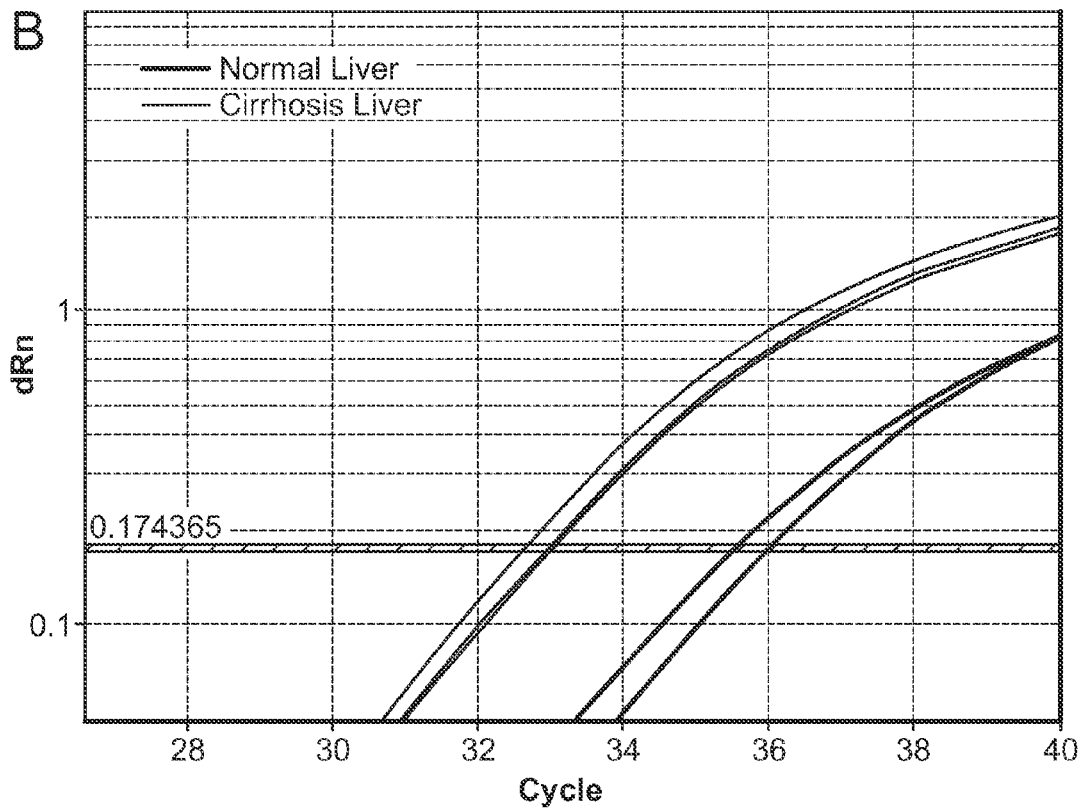
Figure 14:
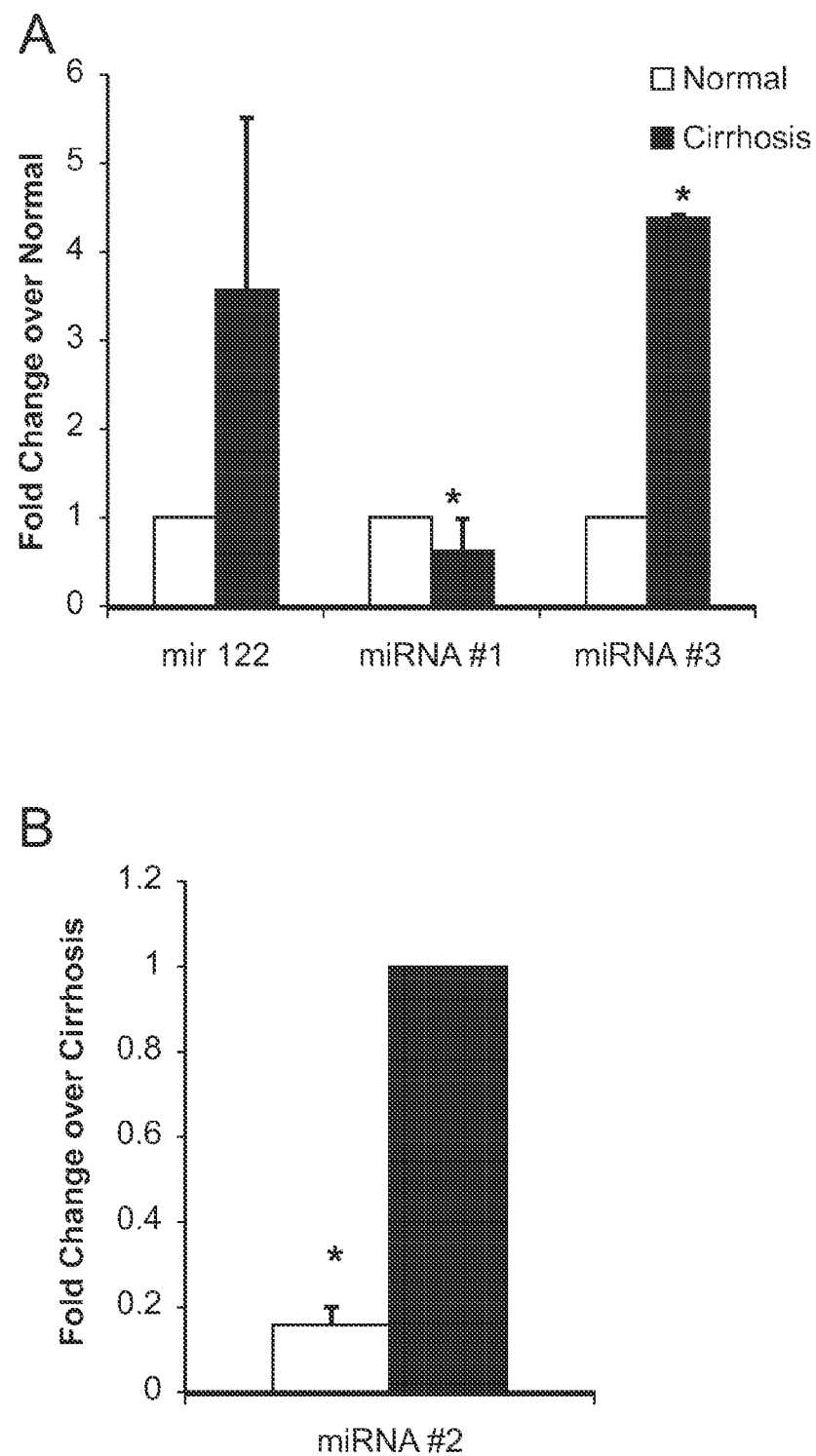
FIGS. 14A and 14B are a panel of graphs demonstrating the level of miRNA #1 (A), #2 (B) and #3 (A) in cirrhotic human liver tissue.
Figure 15:
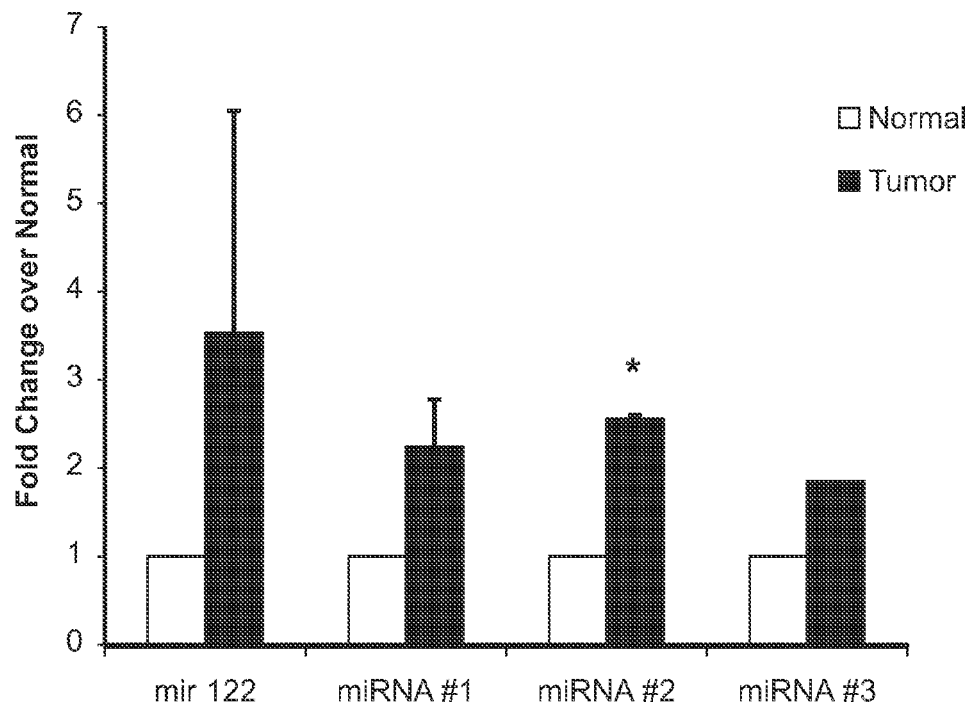
FIG. 15 is a panel of graphs demonstrating the level of miRNA #1, #2 and #3 in HCC liver tissue.
Figure 16:
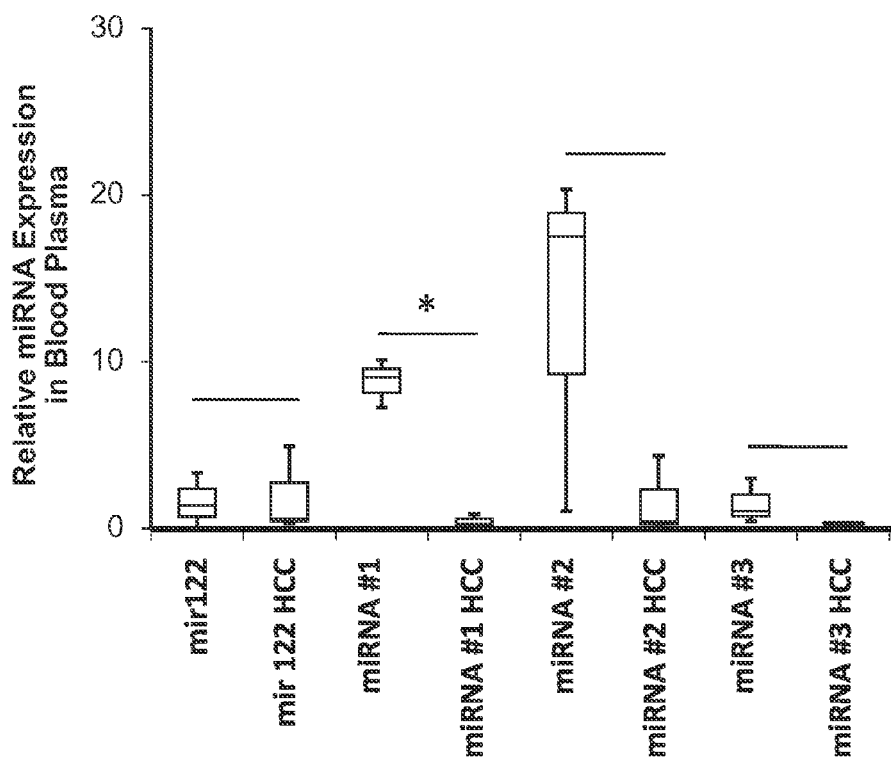
FIG. 16 is a panel of graphs demonstrating the level of miRNA #1, #2 and #3 in the blood plasma of healthy subjects and HCC patients.

RNA mimic molecules were designed and ordered for miRNA #1, #2, #3, and mir-122. It is known that mir-122 inhibits the cancer-linked protein Serum Response Factor (SRF) and, to a lesser extent, ADAM10. As seen in the Western Blot shown in FIG. 5B, miRNA #1 inhibited SRF as well as mir-122 when they were separately transfected into human HEP-G2 cells. These results were corroborated by RT-PCR (FIG. 5A). miRNA #2 also shows similarities to published mir-122 function in that a miRNA#2 mimic inhibits ADAM10 upon transfection into HEPG2 cells (FIG. 5C). To determine our novel miRNA's tissue and biofluid expression patterns, highly specific Northern blot and Ligation RT-PCR probes were used. As shown in FIGS. 14 and 15, miRNA #1, #2, and #3 were all expressed in normal liver tissue. Interestingly, all three novel miRNAs showed significant deregulation in two alcohol-related cirrhosis patients with miRNA #1 being significantly down-regulated and miRNA #2 and miRNA #3 being significantly up-regulated (FIG. 14). These results were confirmed by Northern blot for miRNA #1 and #3 (FIGS. 1 and 12). Similarly, expression in healthy and HCC derived liver tissue was also determined. Once again, all of the miRNAs showed differential accumulation in HCC liver tissue (FIG. 15). The level of these miRNAs in blood samples from healthy and HCC suffering patients was determined by RT-PCR (FIG. 16). All four were detected with miRNA #1 showing significant down-regulation in the blood of HCC patients.

Thus, YmirSCAN has been demonstrated here as a powerful tool to identify novel miRNAs associated with diseases. Novel miRNAs identified herein using YmirSCAN can be easily detected in healthy and diseased liver tissue and blood, thus providing a powerful tool for prognosis, diagnosis and therapeutic treatment of liver disease.

Example 4

Expression of miRNA #1 in Normal and Hepatocarcinoma Tissue

TaqMan MicroRNA Reverse Transcription kit was used to generate cDNA from the blood plasma RNA according the manufacturers' recommendations. Briefly, to synthesize the cDNA the following reagents were combined in a 0.1 ml tube: 10 ng RNA, 30 of 5× TaqMan RT primer (U6, miRNA #1 or mir 122), 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pippetting. The RT reaction was performed by incubation for 30 min at 16° C., then 30 min at 42° C. and finally 5 min at 85° C.

The RT product was amplified using TaqMan Universal Master Mix according the manufacturers' recommendations. Briefly, the following were combined in a 0.1 ml tube: 5 µl TaqMan universal master mix, 0.5 µl of TaqMan Assay (U6, miRNA #1 or mir122), 1 µl of cDNA template and 3.50 of nuclease free water. The samples were gently mixed by pipetting, centrifuged briefly and loaded into the real-time PCR system. The PCR reaction was carried out as follows: polymerase activation for 5 min at 85° C., then amplification over 40 cycles at 95° C. for 15sec and at 60° C. for 1 min.

miRNA #1 is up-regulated (57.5%, p<0.05) in HCC as compared to normal tissue. mir-122 is also up-regulated in HCC tissue (353.6%), however not statistically significant manner (FIG. 15).

Example 5

MiRNA #1 Targets Serum Reduced Factor (SRF)

HepG2 cells were transfected with miRNA #1, mir122 or control mimic. 24hr after transfection RNA was isolated from the samples as follows. 1 ml of TRIzol reagent was added to each well and incubated on ice for 10 min. The lysates were collected with a cell scraper and 0.3 ml of chloroform was added to the samples. The samples were vigorously shaken and centrifuged at 4° C. for 15 min at 12,000×g. The aqueous phase containing the RNA was removed and placed in a separate container. 0.5 ml of isopropyl alcohol was added to the samples and the samples were incubated on ice for 10 min. The samples were centrifuged at 12,000×g for 10 min at 4° C. The supernatant was removed and the samples were washed once with 1 ml of 80% ethanol. The supernatant was removed and the samples were air dried for 10 min and resuspended in 50 µl of nuclease free water.

TaqMan MicroRNA Reverse Transcription kit was used to generate cDNA from the isolated normal urine RNA according the manufacturers' recommendations. Briefly, to synthesize the cDNA the following reagents were combined in a 0.1 ml tube: 50 RNA, 30 of 5× TaqMan RT primer, 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pipetting. The RT reaction was performed by incubation for 30 min at 16° C., then 30 min at 42° C. and finally 5 min at 85° C.

High Capacity cDNA RT Kit was used to generate cDNA from the purified RNA samples according the manufacturers' recommendations. Briefly, to synthesize the cDNA the following reagents were combined in a 0.1 ml tube: 5 µl RNA, 1 µl random primers, 1 µl of 10×RT buffer, 0.4 µl 100 mM dNTP, 0.5 µl Multiscribe RT enzyme, nuclease free water to 10 µl. The RT reaction was performed by incubation for 10 min at 25° C., then 120 min at 37° C. and finally 5 min at 85° C.

The RT product from TaqMan MicroRNA Reverse Transcription kit was amplified using TaqMan Universal Master Mix according the manufacturers' recommendations. Briefly, the following reagents were combined in a 0.1 ml tube: 50 TaqMan universal master mix, 0.5 µl of TaqMan Assay, 1 µl of cDNA template and 3.50 of nuclease free water. The samples were gently mixed by pipetting, centrifuged briefly and loaded into the real-time PCR system. The PCR reaction was carried out as follows: polymerase activation for 5 min at 85° C., then amplification over 40 cycles at 95° C. for 15sec and at 60° C. for 1 min.

The RT product from High Capacity cDNA RT Kit was amplified using Power SybrGreen PCR Master Mixx according the manufacturers' recommendations. Briefly, the following reagents were combined in a 0.1 ml tube: 50 Poer SyrbGreen master mix, 30 of 2.66 mM mix of forward and reverse primers (i.e., 2.60 of 100 mM reverse+2.60 of 100 mM forward primer, nuclease free water to 100 µl of nuclease free water. The samples were gently mixed by pipetting, centrifuged briefly and loaded into the real-time PCR system. The PCR reaction was carried by first activating polymerase for 10 min at 95° C., then amplification over 40 cycles at 95° C. for 15sec and at 60° C. for 1 min. For serial dilution cDNA template was diluted 10 fold in water then 20 were added to the reaction.

Data was analyzed by normalizing threshold cycles (cT) of all samples to 18S—which is not expected to vary- and calibrated to control samples [deltaCt analysis].

Figure 5A:
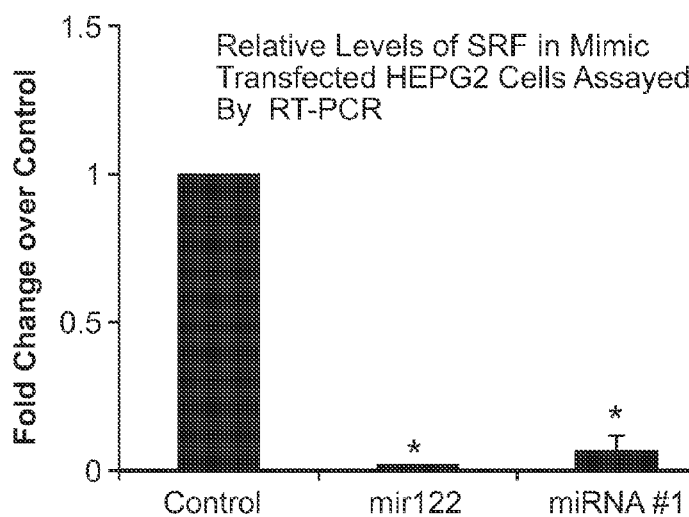
FIG. 5A is a graph showing relative levels of the cancer-linked protein serum response factor (SRF) in mimic transfected HEPG2 cells assayed by RT-PCT. miRNA #1 inhibits SRF.
Figure 5A:
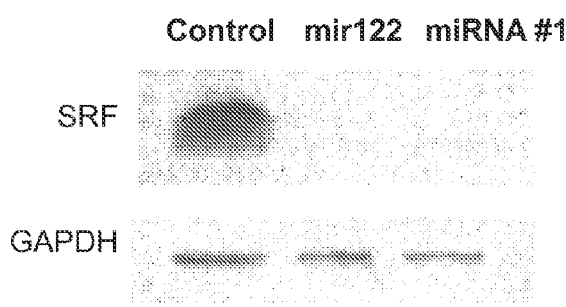
Figure 5A:
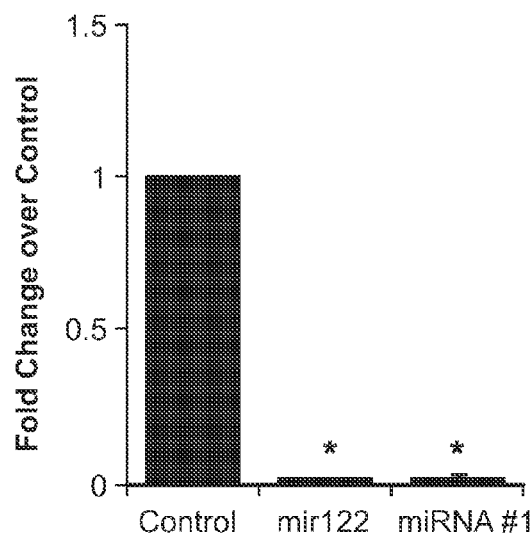
Figure 5C:
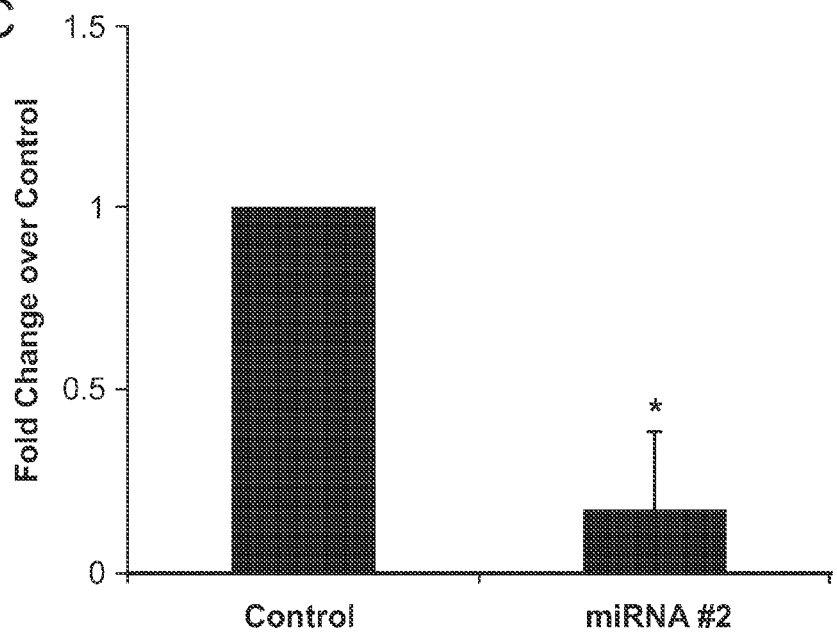
FIG. 5C is a graph showing that miRNA#2 inhibits cancer-linked protein ADAM10.
Figure 6:
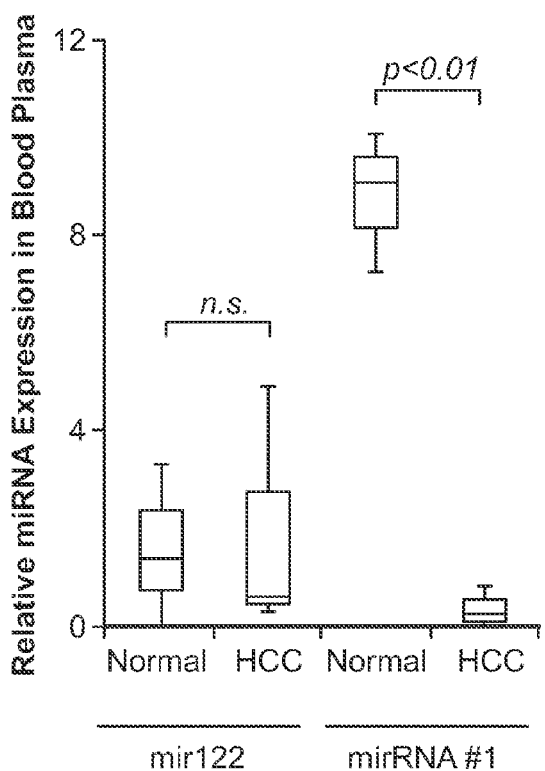
FIG. 6 is a graph demonstrating significant difference of miRNA #1 level in normal and HCC blood sample.

As detected by both Western Blot and RT-PCR, transfection of miRNA #1 and mir-122 mimics induce a statistically significant reduction (97%) of expression of serum response factor (SRF; 1 v 0.063±0.059, n=2, p<0.01) (FIGS. 5A and 5B).

Example 6

Expression of miRNA #1 in Human Normal and Hepatocarcinoma Blood Plasma

RNA was isolated from blood plasma samples using mirVANA Paris Kit following manufacturers' suggestions. 0.25 ml of blood plasma was combined with 0.25 ml of 2× Denaturing Solution then with 0.5 ml of acid-phenol: chloroform. After vortexing the samples were centrifuged for 5 min at 10,000×g at RT. The aqueous phase was removed and combined with ⅓ ethanol by volume. The solution was passed though the filter and the filtrate was combined with ⅔ ethanol by volume. The solution was passed through the filter and washed once with 0.7 ml wash solution 1 then twice with 0.5 ml wash solution ⅔. The bound RNA was finally eluted with 0.1 ml nuclease free water.

TaqMan MicroRNA Reverse Transcription kit was used to generate cDNA from the blood plasma RNA according the manufacturers' recommendations. Briefly, to synthesize the cDNA the following reagents were combined in a 0.1 ml tube: 50 RNA (diluted 1:10 in nuclease free water), 30 of 5× TaqMan RT primer (miRNA #1 or mir 122), 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pipetting. The RT reaction was performed by incubation for 30 min at 16° C., then 30 min at 42° C. and finally 5 min at 85° C.

To detect the 18S contol, High Capacity cDNA RT Kit was used to generate cDNA from the purified RNA samples according the manufacturers' recommendations. Briefly, to synthesize the cDNA the following reagents were combined in a 0.1 ml tube: 50 RNA (diluted 1:10 in nuclease free water), 1 µl random primers, 1 µl of 10×RT buffer, 0.4 µl 100 mM dNTP, 0.5 µl Multiscribe RT enzyme, nuclease free water to 104 The RT reaction was performed by incubation for 10 min at 25° C., then 120 min at 37° C. and finally 5 min at 85° C.

The RT product was amplified using TaqMan Universal Master Mix according the manufacturers' recommendations. Briefly, the following reagents were combined in a 0.1 ml tube: 50 TaqMan universal master mix, 0.5 µl of TaqMan Assay (miRNA #1, 18S or mir122), 1 µl of cDNA template and 3.50 of nuclease free water. The samples were gently mixed by pipetting, centrifuged briefly and loaded into the real-time PCR system. The PCR reaction was carried out as follows: polymerase activation for 5 min at 85° C., then amplification over 40 cycles at 95° C. for 15sec and at 60° C. for 1 min.

Data was analyzed by normalizing threshold cycles (cT) of all samples to 18S—which is not expected to vary [deltaCt analysis].

miRNA #1 is expressed in both the normal (8.81±0.83) and hepatocarcinoma (0.37±0.25) blood plasma. miRNA #1 downregulation is statistically significant with p=0.0006.

Example 7

Expression of miRNA #1 in Normal and Cirrhosis Tissue

TaqMan MicroRNA Reverse Transcription kit was used to generate cDNA from normal and cirrhosis tissue RNA according the manufacturers' recommendations. Briefly, to synthesize the cDNA the following reagents were combined in a 0.1 ml tube: 1Ong RNA, 3 µl of 5× TaqMan RT primer (U6, miRNA #1 or mir 122), 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pippetting. The RT reaction was performed by incubation for 30 min at 16° C., then 30 min at 42° C. and finally 5 min at 85° C.

The RT product was amplified using TaqMan Universal Master Mix according the manufacturers' recommendations. Briefly, the following reagents were combined in a 0.1 ml tube: 50 TaqMan universal master mix, 0.5 µl of TaqMan Assay (U6, miRNA #1 or mir122), 1 µl of cDNA template and 3.50 of nuclease free water. The samples were gently mixed by pipetting, centrifuged briefly and loaded into the real-time PCR system. The PCR reaction was carried out as follows: polymerase activation for 5 min at 85° C., then amplification over 40 cycles at 95° C. for 15 sec and at 60° C. for 1 min.

Figure 4:
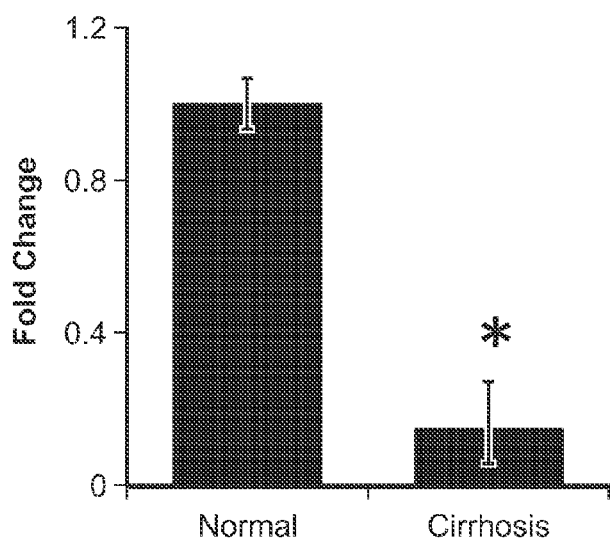
FIGS. 4A and 4B are a panel of graphs demonstrating that miRNA #1 is detected by ligation RT-PCR in normal and cirrhotic liver.
Figure 4:
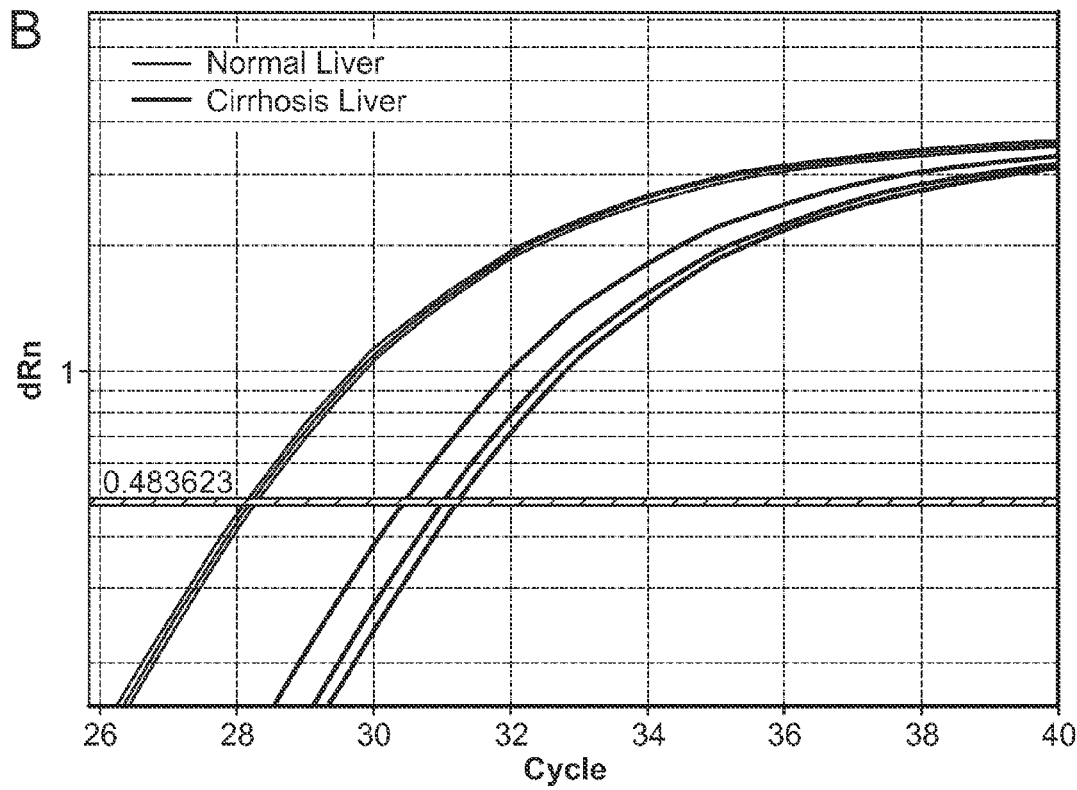

Data was analyzed by normalizing threshold cycles (cT) of all samples to U6—which is not expected to vary—and calibrated to normal samples [deltadeltaCt analysis].

miRNA #1 is down-regulated (1 v 0.175±0.028, n=2, p<0.05) in cirrhosis as compared to normal tissue. mir122 levels do not change in a statistically significant manner between normal and cirrhosis tissues (FIGS. 4 and 14).

Example 8

Expression of miRNA #2 in Normal and Cirrhosis Tissue

TaqMan MicroRNA Reverse Transcription kit was used to generate cDNA from normal and cirrhosis tissue RNA according the manufacturers' recommendations. Briefly, to synthesize the cDNA the following reagents were combined in a 0.1 ml tube: 10 ng RNA, 30 of 5× TaqMan RT primer (U6, miRNA #2 or mir 122), 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pippetting. The RT reaction was performed by incubation for 30 min at 16° C., then 30 min at 42° C. and finally 5 min at 85° C.

TaqMan MicroRNA Reverse Transcription kit was used to generate cDNA from normal and cirrhosis tissue RNA according the manufacturers' recommendations. Briefly, to synthesize the cDNA the following reagents were combined in a 0.1 ml tube: 10 ng RNA, 3 µl of 5× TaqMan RT primer (U6, miRNA #2 or mir 122), 1.50 of 10×RT buffer, 0.19 µl RNAse inhibitor, 4.16 µl nuclease free water, 0.15 µl 100 mM dNTP, 1 µl Multiscribe RT enzyme. The sample was mixed by pippetting. The RT reaction was performed by incubation for 30 min at 16° C., then 30 min at 42° C. and finally 5 min at 85° C.

Figure 10:
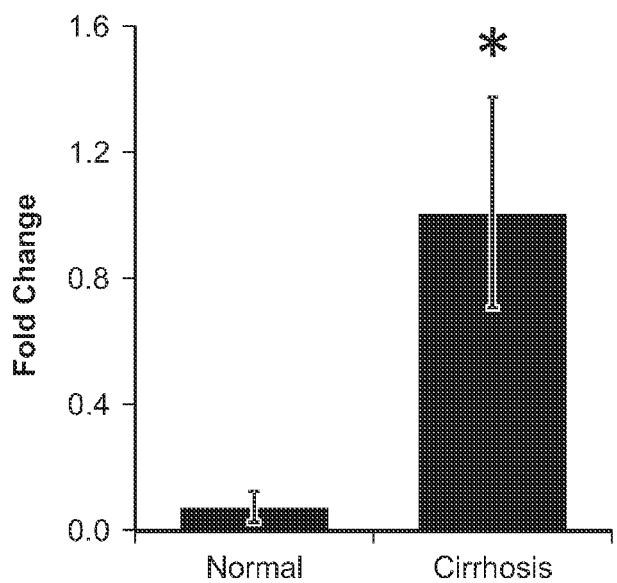
FIGS. 10A and 10B are a panel of graphs demonstrating detection of miRNA #2 by ligation RT-PCR in normal and cirrhotic liver.
Figure 10:
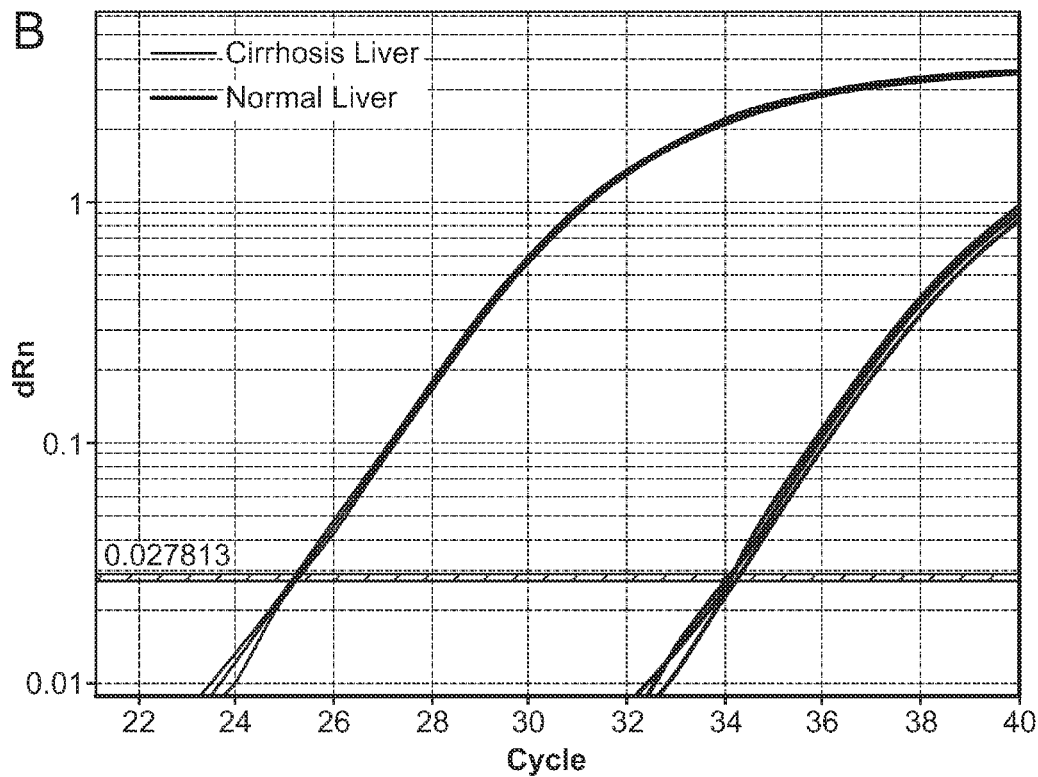
Figure 11:
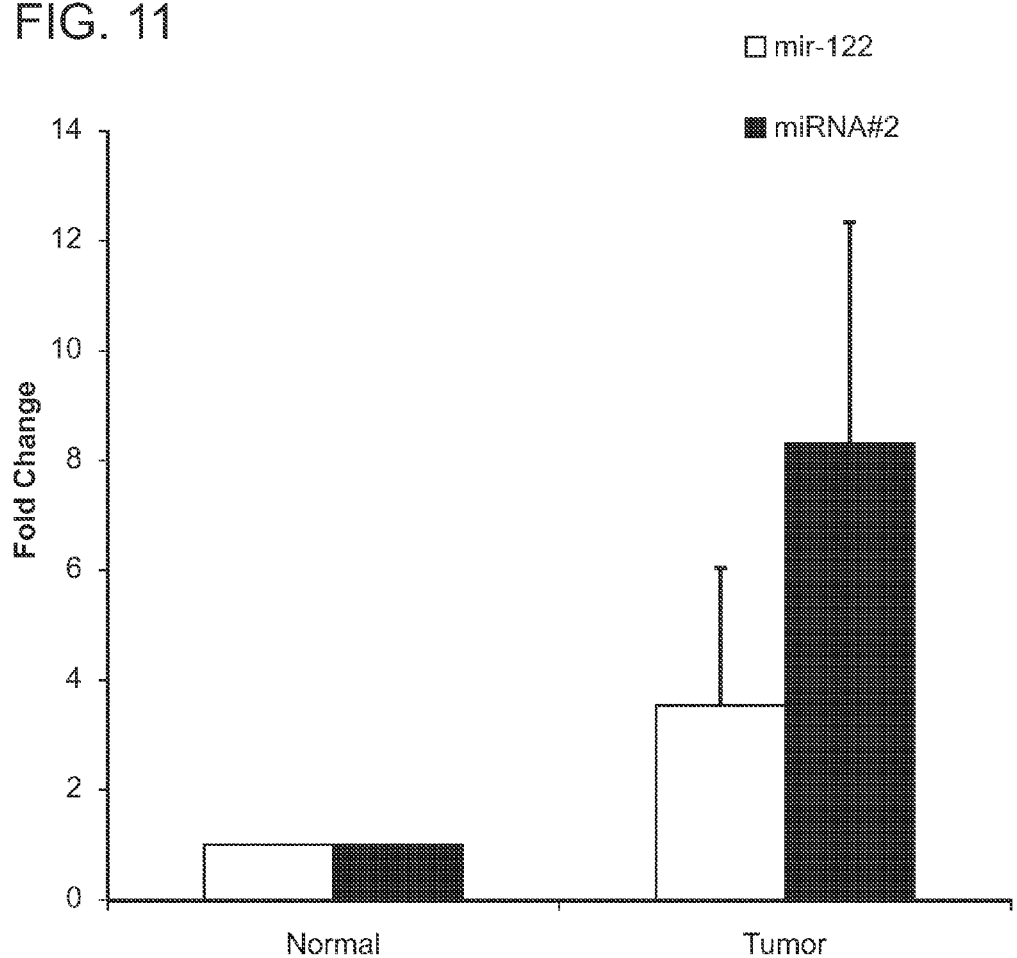
FIG. 11 is a graph demonstrating the expression of miRNA #2 in normal and HCC liver tissue.

Data was analyzed by normalizing threshold cycles (cT) of all samples to U6—which is not expected to vary—and calibrated to normal samples [deltadeltaCt analysis].

miRNA #2 is up-regulated in cirrhosis tissue as compared to normal tissue (0.14±0.075 v 1, n=2, p<0.05). mir122 levels do not change in a statistically significant manner between normal and cirrhosis tissues (FIGS. 10 and 14).

Example 9

Expression of miRNA #3 in normal and Alcoholic Fatty Acid Liver Disease samples 3 plasma samples from healthy individuals and 2 plasma samples from patients suffering from Alcoholic Fatty Acid Liver Disease were analyzed with PCR primers specific for miRNA #3, 451 and 122.

Under these conditions, miRNA #3 could not be detected in the healthy samples but could be detected in the AFLD samples while miRNAs 451 and 122 are relatively constant in all samples.

Thus, miRNA #3 could potentially be used to distinguish samples of AFLD suffers versus healthy. Data shown in Table 1 is PCR cycles. The lower number the higher the concentration.

TABLE 1

| Patient Type | miRNA #3 | miRNA 451 | miRNA 122 |
| --- | --- | --- | --- |
| Normal 1 | ND | 23.97 +/− 0.38 | 29.70 +/− 0.33 |
| Normal 2 | ND | 24.63 +/− 0.36 | 30.66 +/− 0.34 |
| Normal 3 | ND | 24.50 +/− 0.18 | 31.37 +/− 0.60 |
| AFLD 1 | 36.48 +/− 0.45 | 25.92 +/− 0.08 | 31.21 +/− 0.04 |
| AFLD 2 | 36.64 +/− 0.75 | 25.86 +/− 0.06 | 30.96 +/− 0.06 |

ND = Not Detected
AFLD = Alcoholic Fatty Acid Liver Disease

We claim:

1. A method of identifying a novel microRNA (miRNA) comprising
   (a) searching in a deep sequencing database using a seed sequence of a known miRNA that is associated with at least one disease, wherein the seed sequence consists of at least 6 nucleotides;
   (b) identifying a read sequence in the deep sequencing database, wherein 0 or 1 mismatch exists when the seed sequence is aligned against the first 12 non-adaptor nucleotides at the 5' end of the read sequence;
   (c) searching human genome database using a fragment of the read sequence consisting of the seed sequence and 10-12 nucleotides of the read sequence extended from the 3' end of the seed sequence;
   (d) identifying in the human genome database a target sequence, wherein the fragment of the read sequence 100% matches the target sequence;
   (e) determining the presence of a hairpin in a query sequence, wherein the query sequence consists of the fragment of the read sequence and 50-100 nucleotides of the target sequence extended from both the 5' and 3' ends of the fragment of the read sequence;
   (f) determining the position of the seed sequence relative to the terminal loop of the hairpin within the query sequence when the hairpin is present; and
   (g) identifying a novel miRNA sequence, wherein the seed sequence is 20-35 nucleotides upstream or 0-10 nucleotides downstream of the terminal loop of the hairpin.

2. The method of claim 1 wherein the seed sequence consists of the nucleotide sequence of SEQ ID NO: 8.

* * * * *